United States Patent
Gord et al.

[11] Patent Number: 5,999,849
[45] Date of Patent: *Dec. 7, 1999

[54] LOW POWER RECTIFIER CIRCUIT FOR IMPLANTABLE MEDICAL DEVICE

[75] Inventors: John C. Gord, Venice; Lyle Dean Canfield, Lake Hughes, both of Calif.

[73] Assignee: Alfred E. Mann Foundation, Santa Clarita, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/928,871

[22] Filed: Sep. 12, 1997

[51] Int. Cl.$^6$ .............................. A61N 1/08; H02M 7/217
[52] U.S. Cl. ................................ 607/2; 327/104; 363/127
[58] Field of Search ..................................... 327/104, 124; 607/2, 36, 122, 116, 5, 35; 600/373, 377; 363/127

[56] References Cited

U.S. PATENT DOCUMENTS

| | | |
|---|---|---|
| 3,434,034 | 3/1969 | Garber et al. . |
| 4,086,624 | 4/1978 | Fraley ........................................ 363/127 |
| 4,507,525 | 3/1985 | Siligoni et al. . |
| 4,535,203 | 8/1985 | Jenkins et al. ........................... 363/127 |
| 4,671,288 | 6/1987 | Gough . |
| 4,704,545 | 11/1987 | Tanaka et al. . |
| 5,411,528 | 5/1995 | Miller et al. . |
| 5,497,772 | 3/1996 | Schulman et al. . |
| 5,510,972 | 4/1996 | Wong . |
| 5,540,729 | 7/1996 | Weijand ..................................... 607/35 |
| 5,691,658 | 11/1997 | Klein ........................................ 327/104 |
| 5,825,214 | 10/1998 | Klosa . |

FOREIGN PATENT DOCUMENTS

| | | |
|---|---|---|
| 0 791 706 A1 | 8/1997 | European Pat. Off. . |
| WO 89/05058 | 6/1989 | WIPO . |

Primary Examiner—William E. Kamm
Assistant Examiner—Carl H. Layno
Attorney, Agent, or Firm—Abraham N. Seidman; Bryant R. Gold

[57] ABSTRACT

A low power switched rectifier circuit is realized using P-MOS and N-MOS FET switches that are turned ON/OFF at just the right time by a detector and inverter circuit (which form an integral part of the rectifier circuit) to rectify an incoming ac signal in a highly efficient manner. Parasitic diodes and transistors that form an integral part of the FET circuitry respond to and rectify the incoming signal during start up, i.e., when no supply voltage is yet present, thereby providing sufficient operating voltage for the FET switches to begin to perform their intended rectifying function. In the absence of an incoming ac signal, i.e., during the time between biphasic pulses, the rectifier circuit is biased with an extremely small static bias current; but in the presence of an incoming ac signal, at a time when the positive and negative phases of the incoming signal are to be connected to positive and negative supply lines, a much larger dynamic bias current is automatically triggered.

23 Claims, 11 Drawing Sheets

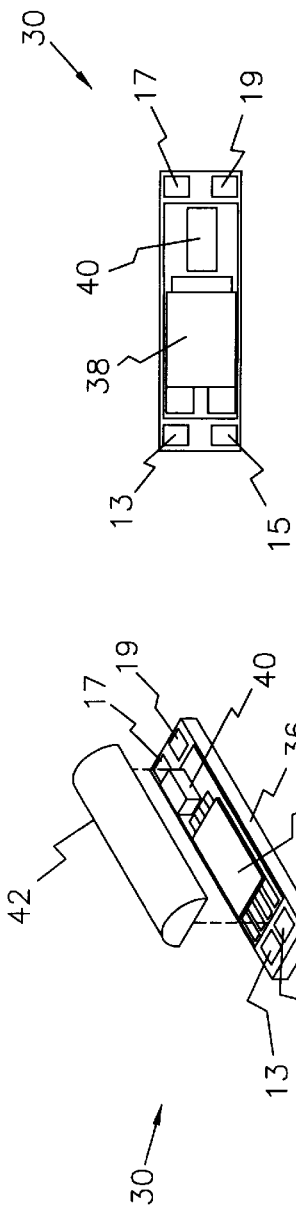
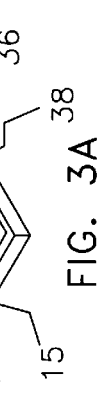
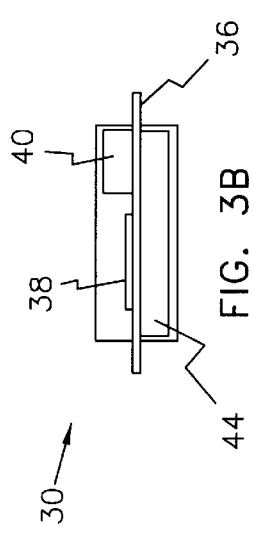
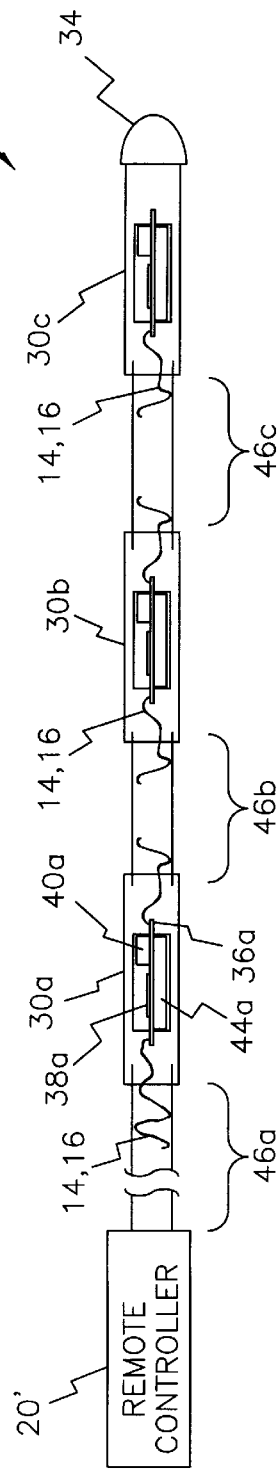

LOW POWER RECTIFIER CIRCUIT FOR IMPLANTABLE MEDICAL DEVICE

FIELD OF THE INVENTION

The present invention relates to implantable medical devices, and more particularly to a very-low power rectifier circuit that may be used within an implantable sensor or similar device to rectify low level pulsed or ac signals so that the energy contained in such signals can be converted to a dc potential which provides operating power for other circuits of the implantable device.

BACKGROUND OF THE INVENTION

In the implantable medical device field, a medical device, configured to perform a desired medical function, is implanted in the living tissue of a patient so that a desired function may be carried out as needed for the benefit of the patient. Numerous examples of implantable medical devices are known in the art, ranging from implantable pacemakers, cochlear stimulators, muscle stimulators, glucose sensors, and the like.

Some implantable medical devices are configured to perform the sensing function, i.e., to sense a particular parameter, e.g., the amount of a specified substance in the blood or tissue of the patient, and to generate an electrical signal indicative of the quantity or concentration level of the substance sensed. Such electrical signal is then coupled to a suitable controller, which may or may not be implantable, and the controller responds to the sensed information in a way to enable the medical device to perform its intended function, e.g., to display and/or record the measurement of the sensed substance. An example of an implantable medical device that performs the sensing function is shown, e.g., in U.S. Pat. No. 4,671,288.

As medical devices have become more useful and numerous in recent years, there is a continual need to provide very low power sensors that may be connected to, or incorporated within, such devices so that the desired function of the device can be carried out without the expenditure of large amounts of power (which power, for an implanted device, is usually limited.)

It is known in the art to inductively couple a high frequency ac signal into an implanted medical device to provide operating power for the circuits of the device. Once received within the implanted device, a rectifier circuit, typically a simple full-wave or half-wave rectifier circuit realized with semiconductor diodes, is used to provide the rectifying function. Unfortunately, when this is done, a significant signal loss occurs across the semiconductor diodes, i.e., about 0.7 volts for silicon, which signal loss represents lost power, and for low level input signals of only a volt or two represents a significant decrease in the efficiency of the rectifier.

For the extremely low power implantable devices and sensors that have been developed in recent years, low operating voltages, e.g., 2–3 volts, are preferable in order to keep overall power consumption low. Unfortunately, with such low operating voltages are used, a diode voltage drop of 0.7 volts represents a significant percentage of the overall voltage, thus resulting in a highly inefficient voltage rectification or conversion process. An inefficient voltage conversion, in turn, translates directly to increased input power, which increased input power defeats the overall design goal of the low power device. What is needed, therefore, is a low power rectifier circuit that efficiently converts a low amplitude alternating input signal to a low output operating voltage.

Further, it is not always possible to fabricate diode-type bridge rectifiers on CMOS or bipolar chips using conventional processing technology. It is particularly difficult to make a good connection with the non-substrate positive rail or positive supply of the chip. There is thus a need in the art for a low power rectifier circuit that generally avoids the use of problematic diodes.

Rather than diodes, switches may be used within a rectifier circuit. Such switches can be configured to exhibit an extremely low turn on voltage, e.g., on the order of 50 mV. Disadvantageously, before such switching circuits can operate, there must be an operating potential already available (supply voltage) that can bias (provide operating power to) the switches for their desired operation. In many implantable sensor applications, an operating potential will not exist until such time as the rectifier circuit rectifies the incoming power signal. Thus, rectification cannot occur until an operating potential is present, and an operating potential cannot exist until rectification occurs—a true stalemate. It is thus evident that critical improvements are needed in the rectification circuits used within low power implantable devices, such as implantable sensors, that are powered by an incoming ac or pulsed signal.

SUMMARY OF THE INVENTION

The present invention addresses the above and other needs by providing a very low power rectifier circuit realized using complementary P-MOS and N-MOS (CMOS) FET switches. The FET switches are turned ON and OFF at just the right time by a control circuit in order to provide the desired rectifying function. The control circuit forms an integral part of the rectifier circuit and consumes very little power.

In accordance with one aspect of the invention, parasitic diodes and transistors form an integral part of the control/rectifier circuit. Such parasitic elements, normally a problem in an integrated circuit, respond to and rectify the incoming power signal when the incoming signal is first received, i.e., when no supply voltage is yet present, thereby providing a startup operating voltage to the CMOS FET switches so that they can begin to perform their intended rectifying function.

In accordance with another aspect of the invention, the CMOS FET switches are automatically switched ON and OFF by the control circuit at appropriate times by an incoming pulsed power signal so as to keep the power consumption of the rectifier circuit at a minimum level. More particularly, in the absence of an incoming pulse, i.e., during the time inbetween pulses (which, from a duty cycle point of view, represents the vast majority of the total time), the rectifier circuit is biased with an extremely small static bias current; but in the presence of an incoming pulse, i.e., at the time when the pulses are actually being received (which, from a duty cycle point of view, represents a very small portion of the total time), a much larger dynamic bias current is triggered. Using two levels of bias current in this fashion permits a highly efficient operation of the CMOS FET switches as the desired rectification function is automatically carried out.

In accordance with yet another aspect of the invention, the low power rectifier circuit may be included within the hermetically-sealed portion of an implantable sensor that includes both a non-hermetically sealed part (containing, e.g., electrodes, connection terminals, and/or sensor materials that must be in contact with body fluids or tissue) and an hermetically sealed part (containing electrical circuitry, including the rectifier circuit of the present invention, to manage, monitor and/or control the non-hermetically sealed part). A first pair of terminals is included as part of the non-hermetically sealed part and functions as the input/output terminals for connecting the implantable sensor to an implantable medical device over a connection bus that includes just two conductors, one conductor being connected to each terminal. Both operating power and control data are transmitted over the two-conductor bus from the medical device to the sensor; and sensed data is transmitted over the same two-conductor bus from the implantable sensor to the medical device. The first pair of terminals (or a second pair of terminals electrically connected to the first pair of terminals), may also function as connection terminals for attaching additional implantable sensors to the connection bus, in daisy-chain fashion, as disclosed in applicant's copending patent, entitled DAISY-CHAINABLE SENSORS AND STIMULATORS FOR IMPLANTATION IN LIVING TISSUE, Ser. No. 08/928,867, filed Sep. 12, 1997 (Attorney Docket No. 56287), incorporated herein by reference.

It is thus a feature of the present invention to provide a very low power, implantable, switched rectifier circuit for use within an implantable sensor or other device, e.g., an implantable glucose sensor, that exhibits a very low turn on voltage, e.g., on the order of 50 mV, and that can startup and operate from the incoming ac or pulsed power signal even when no previously stored operating voltage is present.

It is another feature of the invention to provide a highly efficient, switched rectifier circuit exhibiting very low turn on voltages for use with implantable medical devices or other low power devices.

It is a further feature of the invention to provide such a low power rectifier circuit that is self starting, i.e., that responds to an incoming ac or pulsed power signal, such as a pulse train of biphasic pulses, even when no operating voltage is currently present.

It is an additional feature of the invention to provide such a low power rectifier circuit that self-generates all the necessary control signals to turn the rectifying switches ON and OFF at the appropriate time as a function of the incoming ac signal.

It is yet a further feature of the invention to provide a low power rectifier circuit that operates using a very low static bias current most of the time when the circuit is operating, but which automatically triggers a larger dynamic bias current during those times when an incoming pulse is present, which dynamic bias current from a duty cycle point of view is typically present for only a small portion of the total operating time.

BRIEF DESCRIPTION OF THE DRAWINGS

The above and other aspects, features and advantages of the present invention will be more apparent from the following more particular description thereof, presented in conjunction with the following drawings wherein:

FIG. 3A shows a perspective, partially exploded, view of a sensor of the type used in the daisy chain of FIG. 2;

FIG. 3B illustrates a sectional side view of the sensor of FIG. 3A;

FIG. 3C illustrates a sectional top view of the sensor of FIG. 3A;

FIG. 3D illustrates a sectional end view of the sensor of FIG. 3A;

FIG. 4 depicts an implantable lead that includes a plurality of the sensors of FIGS. 3A–3D;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The present invention relates to a very low power, highly efficient, rectifier circuit particularly suitable for use within implantable medical devices or other electrical devices wherein operating power is obtained from a received low level ac or pulsed signal, and wherein power consumption of the device is minimized as much as possible. The description of such rectifier circuit is described more fully below in connection with FIGS. 9–13.

The rectifier circuit provided by the present invention is especially well suited for use within an implantable sensor of the type described in connection with FIGS. 1–8. It is to be understood, however, that the invention is not limited to use only within sensors of the type described in connection with in FIGS. 1–8; rather the sensors and sensor systems of the type described in connection with FIGS. 1–8 merely represent the best mode currently contemplated for using such rectifier circuit.

A thorough understanding of the sensors and sensor systems illustrated in FIGS. 1–8 should not be necessary to appreciate and understand the salient features of the rectifier circuit described herein. Nonetheless, because a general understanding of such sensors and sensor systems may provide useful background information relative to one way the invention may be used, and because one embodiment of the invention comprises a rectifier circuit as described below in FIGS. 9–13 used within a sensor of the type described in FIGS. 1–8, only a cursory explanation of FIGS. 1–8 will be provided herein. A more thorough description of each of FIGS. 1–8 may be found in applicant's copending patent application entitled: DAISY-CHAINABLE SENSORS AND STIMULATORS FOR IMPLANTATION IN LIVING TISSUE, Ser. No. 08/928,867, filed Sep. 12, 1997 (Attorney Docket No. 56287), incorporated herein by reference.

Overview of the Preferred Implantable Sensors

Figure 1:
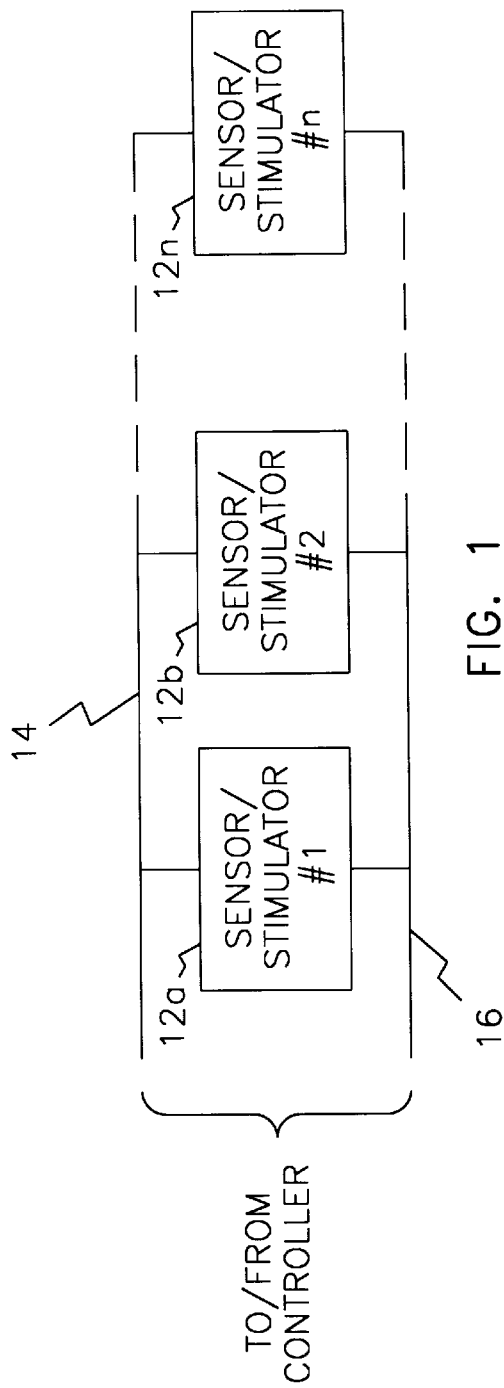
FIG. 1 is a block diagram that illustrates multiple sensors/stimulators connected together using a two-conductor bus, which two-conductor bus may be connected to a controller.

Turning briefly then to FIG. 1, there is shown a block diagram that illustrates multiple sensors 12a, 12b, . . . 12n, or other implantable devices, connected together, as well as a controller (not shown in FIG. 1) using just two common conductors 14 and 16. The two conductors 14 and 16, commonly referred to as a two-conductor connection "bus", provide a common signal and return for data signals and power signals that are sent from the controller to the devices 12a, 12b, . . . 12n, as well as a common signal and return path for data signals transmitted from the devices 12a, 12b, . . . 12n, to the controller.

Figure 2:
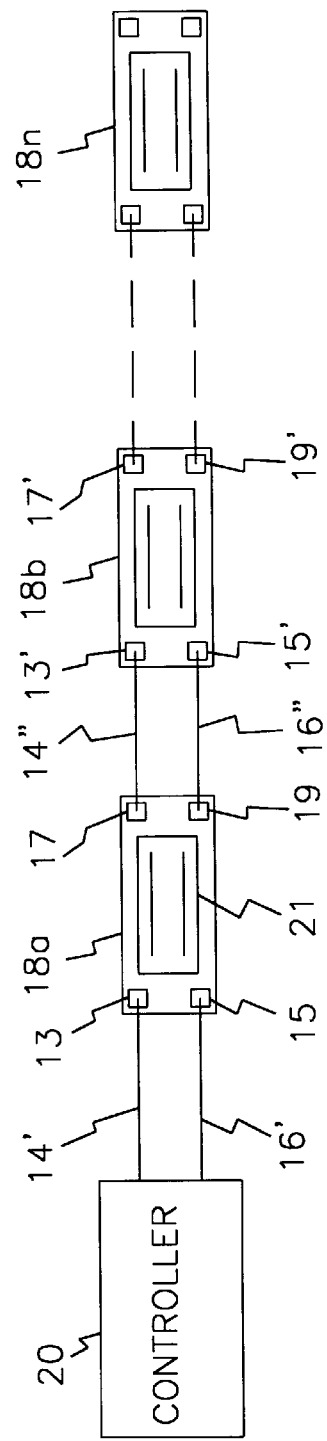
FIG. 2 schematically illustrates a preferred manner of how a sensor made in accordance with the present invention may be connected with a controller and other sensors in a serial or daisy-chain fashion.

FIG. 2 schematically illustrates how an implantable sensor/stimulator 18a be connected with a remote controller 20 and other implantable devices 18b, . . . 18n, in a serial or daisy-chain fashion. As seen in FIG. 2, the device 18a is connected to the controller 20 by two conductors 14' and 16' of the connection bus, which are attached to a first pair of pads or terminals 13 and 15 along a proximal side (i.e, the side closest to the controller 20) of the device 18a. Another pair of pads or terminals 17 and 19 are located along a distal side (i.e., the side farthest from the controller 20) of the device 18a. The distal pad 17 is electrically connected to the proximal pad 13 through the circuitry 21 located on the device 18a. Similarly, the distal pad 19 is electrically connected to the proximal pad 15 through the circuitry 21 included within the device 18a. Two additional conductors 14" and 16" are then used to connect the distal pads 17 and 19 of the device 18a to corresponding proximal pads 13' and 15' of the next device 18b connected in the daisy chain. In this manner, as many devices as desired may be serially connected to the controlled 20 using just two conductors.

There exist many different applications for the daisy-chainable sensors 12 or 18 illustrated in FIGS. 1 or 2. Generally, where the sensor 12 or 18 is implanted, it is designed to sense one or more body parameters or substances found in body tissue or fluids, e.g., glucose level, blood pH, $O_2$, temperature, or the like. Such measurements can provide valuable information regarding the condition and status of the patient.

Turning next to FIGS. 3A, 3B, 3C and 3D, there are shown, respectively, a perspective exploded view (FIG. 3A), a side view (FIG. 3B), a top view (FIG. 3C), and an end view (FIG. 3D), of a typical implantable sensor device 30 of a type suited for use with the present invention. As seen best in FIG. 3A, the sensor device 30 typically includes a carrier or substrate 36 on which an integrated circuit (IC) 38 and other components, such as a capacitor 40, are mounted. In some embodiments, it should be noted that the carrier or substrate 36 may actually comprise the substrate on which the IC 38 is fabricated; but for purposes of the explanation which follows, it is assumed that a separate substrate or carrier 36 is employed with various circuit elements mounted thereon to form a hybrid circuit. The carrier or substrate has conductive patterns etched or otherwise deposited thereon to interconnect the IC 30, capacitor 40, and any other components to form a hybrid circuit which carries out the desired sensing (or other) function.

All of the components of the hybrid circuit are hermetically sealed within a cavity formed by a lid or cover 42 which is bonded to the substrate 36. Proximal pads or terminals 13 and 15, as well as distal pads or terminals 17 and 19, remain outside of the hermetically sealed part of the hybrid circuit. These proximal and distal pads, however, are electrically connected to the circuitry within the hermetically sealed part through suitable feedthrough connections. One manner of making such feedthrough connection is to use a feedthru connection that passes through the carrier or substrate in the stair-step manner (including both vertical and horizontal segments) disclosed in co-pending patent application, Ser. No. 08/515,559, filed Aug. 16, 1995, entitled "Hermetically-Sealed Electrical Feedthrough For Use With Implantable Electronic Devices", which application is assigned to the same assignee as is the instant application, and which application is incorporated herein by reference.

On the side of the carrier or substrate opposite the hybrid electrical circuitry, a suitable electrochemical sensor 44, or other desired type of sensor or stimulator, may be formed or located. A type of electrochemical sensor that may be used, for example, is the enzyme electrode sensor described in U.S. Pat. No. 5,497,772, incorporated herein by reference, and in particular, in FIGS. 2A, 2B, 2C, 3, 4A and 4B of that patent.

For purposes of the present invention, the precise nature of the sensor 44, or other element used within the device 30, is not critical. All that matters is that the sensor or other element derive its operating power from an incoming pulsed or ac signal.

Signal communication between the hybrid circuit side of the substrate or carrier 36 (which is the top side as the device 30 is oriented in FIG. 3B or FIG. 3D, and which top side includes the hermetically sealed portion of the device) and the sensor side of the device 30 (which is the bottom side as shown in FIG. 3B or 3D) is achieved by way of appropriate hermetically-sealed feedthroughs that pass step-wise from the hybrid (top) side of the device 30 through the substrate or carrier, e.g., in the manner set forth in the above-referenced '559 patent application.

The configuration illustrated in FIG. 2 is especially well-suited where several of the implantable devices are to be daisy-chained together to form a single lead 32, as shown in FIG. 4. As seen in FIG. 4, three sensor-type devices 30a, 30b, and 30c are connected together via lead segments 46a, 46b, and 46c. Each of the lead segments 46a, 46b, and 46c, contain two conductors 14, 16, and may be constructed in any suitable manner, e.g., with the two conductors being spirally wound within the lead segments, and with the spiral windings being encased or covered within a sheath of silicone rubber, as is known in the lead art. A distal cap 34 covers the distal pads of the end, or most-distal, device 30c of the lead 32.

The low power rectifier circuit of the present invention may be included as part of the electrical circuitry contained within, or included as a part of, what is referred to above as the "hybrid circuit portion" of the implantable device 30. In general, such electrical circuitry allows the implantable device 30 to be daisy chained with other similar implantable devices, while still allowing each individual device to be individually addressed, controlled and monitored from a single controller 20. In particular, the rectifier circuit of the present invention efficiently rectifies low level incoming ac signals, e.g., a biphasic pulse train generated by the controller 20, to a suitable operating potential which provides the operating voltage for the circuitry included within the device.

Figure 5A:
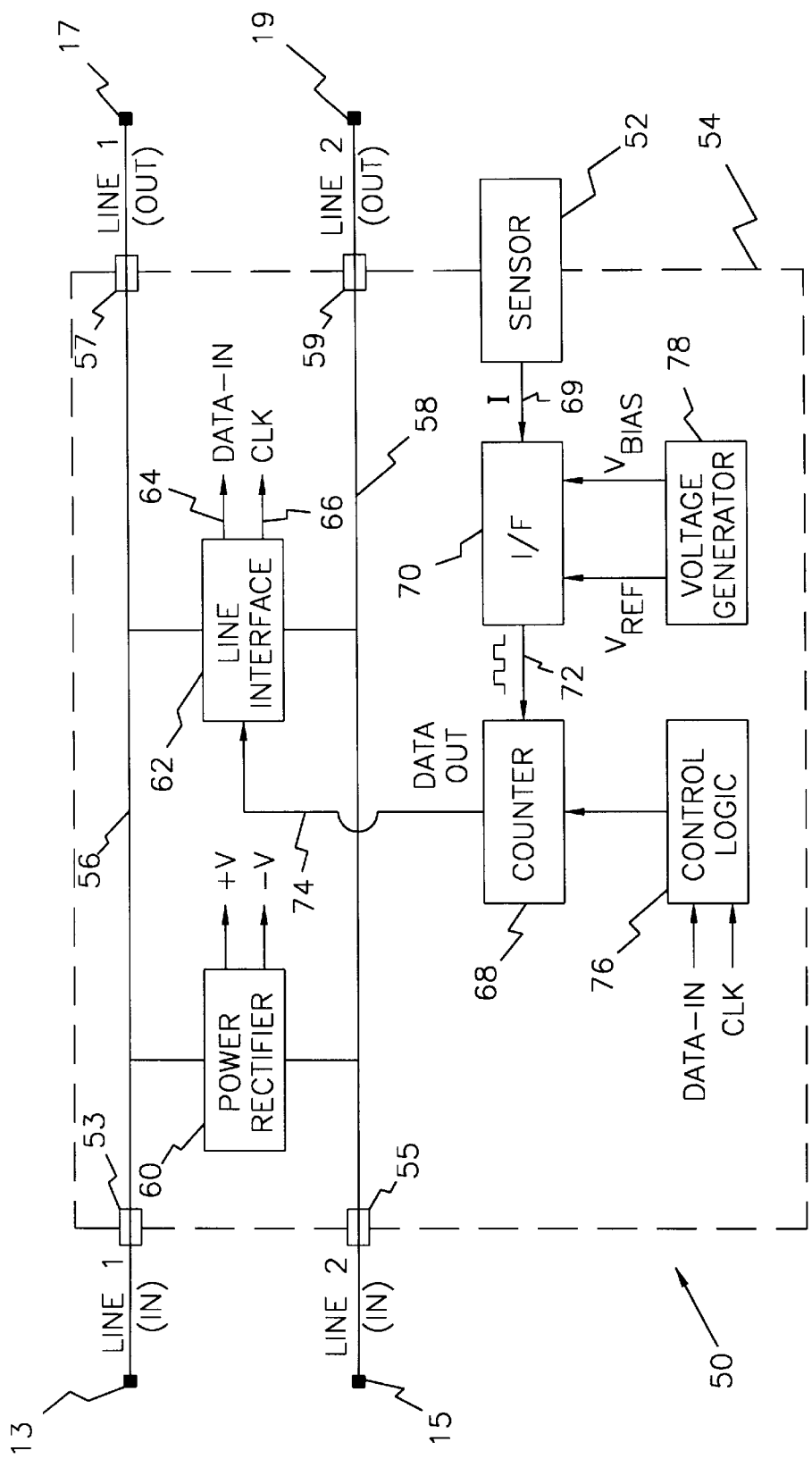
FIG. 5A is a functional block diagram of a simple daisy-chainable implantable sensor that includes a rectifier circuit in accordance with the present invention.
Figure 5B:
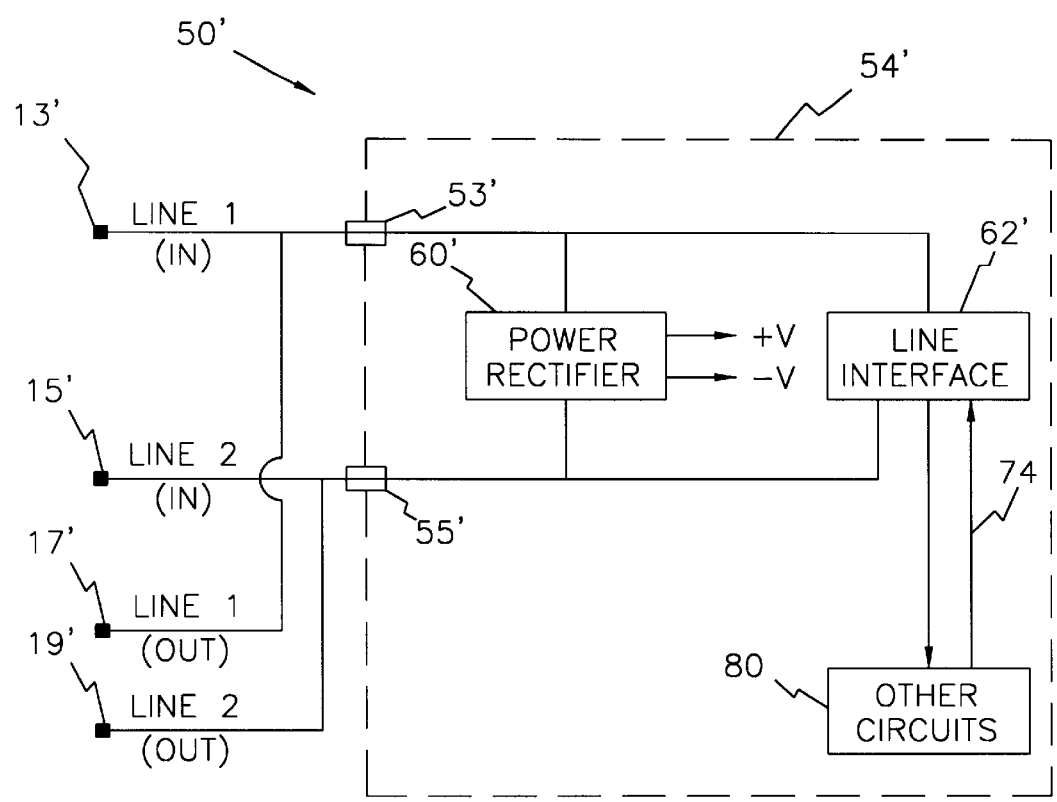
FIG. 5B is a functional block diagram as in FIG. 5A, but wherein an alternate connection scheme is used for attaching additional sensors.
Figure 5C:
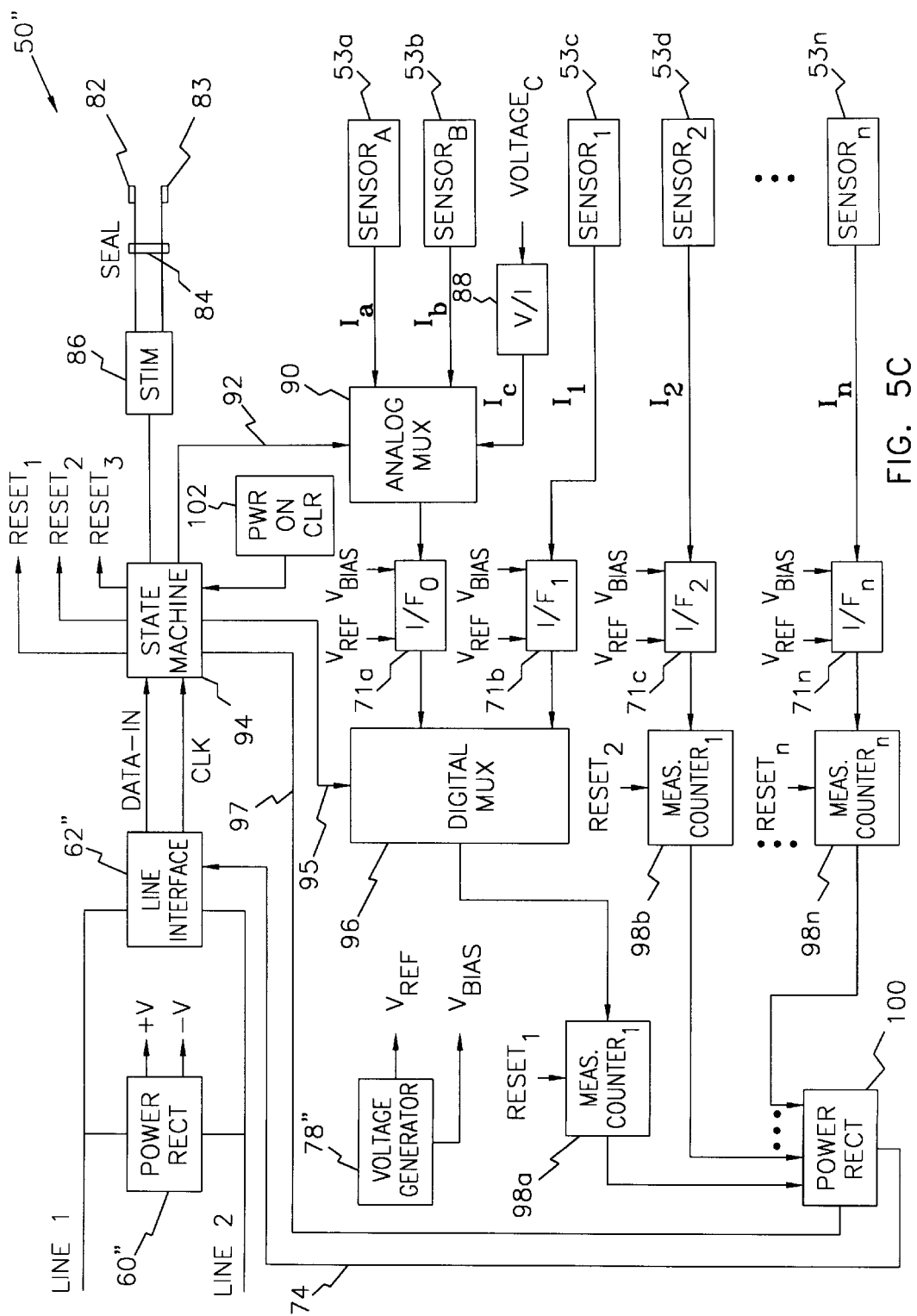
FIG. 5C is a functional block diagram as in FIG. 5A, but wherein additional circuit functions are provided so that a wide variety of different sensors and a stimulator may be included within the same implantable sensor device.

The circuitry included within the hermetically-sealed portion of the device 30 may take many and varied forms. FIGS. 5A, 5B and 5C show three such variations. FIG. 5A, for example, is a functional block diagram of a basic configuration of control/interface circuitry 50 for use with a sensor 52. The dotted line 54 represents an hermetic seal that hermetically seals the circuitry 50 and all but a portion of the sensor 52. The input pads 13 and 15, as well as the output pads 17 and 19, are not hermetically sealed, thereby allowing these pads to be readily connected to the two conductors 14 and 16 (FIG. 1) from the controller 20.

As seen in FIG. 5A, pads 13 and 15 are connected to respective conductive traces, labeled LINE 1 (IN) and LINE 2 (IN), representing the two conductors of the two-conductor bus that connects the device 30 to its controller 20, or to other devices. Each of the LINE 1 and LINE 2 conductive traces passes through respective feedthroughs 53 and 55 into the hermetically sealed portion of the circuitry 50. Pads 17 and 19, on the other side of the circuit, are likewise connected to respective conductive traces, labeled LINE 1 (OUT) and LINE 2 (OUT), and each of these conductive traces passes through respective feedthroughs 57 and 59 into the hermetically sealed portion 54 of the circuitry 50. Inside the hermetically sealed portion, LINE 1 (IN) connects with LINE 1 (OUT) via conductive trace 56, and LINE 2 (IN) connects with LINE 2 (OUT) via conductive trace 58. In this manner, pad 13 is electrically connected with pad 17 via trace 56 which passes through the hermetically sealed portion 54 between feedthroughs 53 and 57. This interconnection of pad 13, trace 56 and pad 57 is referred to hereafter simply as LINE 1. Similarly, pad 15 is electrically connected with pad 19 via trace 58, which trace also passes through the hermetically sealed portion 54 between feedthroughs 55 and 59. This interconnection is referred to hereafter as LINE 2.

As seen in FIG. 5A, a power rectifier circuit 60 is connected between LINE 1 and LINE 2. This rectifier circuit, explained more fully below in conjunction with FIGS. 9–13, extracts and rectifies any signal pulses found on LINE 1 and LINE 2 and produces an operating voltage, +V and −V, for powering the circuitry 50. Such rectification is not a trivial task given the intermittent low level signals which are generally present on LINE 1 and LINE 2. It is this rectifier circuit 60, or an equivalent circuit, that comprises the subject matter of the present invention.

A line interface circuit 62 also is connected between LINE 1 and LINE 2. The circuit 62 functions as an interface between the circuitry 50 and LINE 1 and LINE 2. To this end, the interface circuit 50 receives incoming data pulses present on LINE 1/LINE 2 and generates a DATA-IN signal on line 64 therefrom. The interface circuit 62 further generates a clock (CLK) signal on line 66 that is synchronized with the incoming data signals. The interface circuit 50 also receives digital output data, DATA OUT, from a counter circuit 68, and converts this output data to an appropriate format prior to placing the output data back on LINE 1/LINE 2. One type of line interface circuit 62 that may be used with the circuitry 50 is illustrated in the schematic diagram shown and explained below in conjunction with FIG. 9.

Still referring to FIG. 5A, the sensor 52 may be any suitable sensor adapted to sense a desired condition, parameter, or substance present (or absent) in the implantable tissue within which the device 30 is implanted. For example, the sensor 52 may comprise a glucose sensor that generates an output analog current, I, appearing on line 69, having a magnitude that varies as a function of the sensed glucose.

As a practical matter, regardless of the type of sensor 52 that is employed, it will usually generate either an analog output voltage or an analog output current as a function of the concentration, magnitude, composition, or other attribute, of the parameter being sensed. Such analog current or voltage may then be converted, using an appropriate converter circuit 70, to a frequency signal, appearing on line 72. Typically, the frequency signal on line 72 comprises a train of pulses having a frequency (or repetition rate) that varies as a function of the input voltage or current. In FIG. 5A, for example, it is assumed that the sensor 52 generates an output current I, and that the converter circuit 70 comprises a current-to-frequency (I-to-F) converter circuit, generating an output pulse train on line 72 that has a frequency which varies as the magnitude of the current I varies.

Once a pulse train 72, or other ac signal, is generated having a frequency which varies as a function of the parameter being sensed by the sensor 52, such signal is applied to a counter circuit 68. (Note, as a shorthand notation used in this application, a signal appearing on signal line having a given reference number may be referred to as the signal having such given reference number, i.e., the signal appearing on signal line 72 may simply be referred to as "signal 72".) The counter circuit simply counts the number of pulses present in the signal 72 over a prescribed period of time, e.g., a fixed time window of 1 second, thereby providing a measure of the frequency of the signal 72. In this manner, by resetting the counter 68 at the beginning of each measurement period, the count held in the counter at the end of the measurement period provides a signal representative of the frequency of the signal 72. Such count signal, for the basic embodiment shown in FIG. 5A, may thus serve as the output data signal, DATA OUT, that is sent to the line interface circuit 62 over signal line 74.

Control of the counter 68, i.e., resetting the counter and/or stopping the counter after a prescribed measurement period, is controlled by control logic 76. In a simple embodiment, the measurement period may be a fixed time period. In other embodiments, the measurement period may be set by input data received over signal line 64 from the line interface circuit 62. The clock signal 66 may be used as a measure of elapsed time, as well as to coordinate when the counter 68 sends its DATA OUT signal 74 to the line interface circuit 62.

As needed, a voltage generator circuit 78 (which may form part of the rectifier circuit 60") generates a reference voltage $V_{REF}$, and one or more bias signal(s), $V_{BIAS}$, that are used by the current-to-frequency (I-to-F) converter circuit 70 as it performs its function of converting the analog current signal 69 to a frequency signal 72. Additional details regarding the current-to-frequency converter circuit may be found in applicant's copending patent application Ser. No. 08/928,867, filed concurrently herewith on Sep. 12, 1997 (Attorney Docket No. 57794), entitled LOW POWER CURRENT-TO-FREQUENCY CONVERTER CIRCUIT FOR USE IN IMPLANTABLE SENSORS, assigned to the same assignee as the present application, which application is incorporated herein by reference.

In a similar manner, one or more I-to-F converter circuits may be used within the devices illustrated in FIGS. 5B and 5C, as described in the above-referenced copending patent application, entitled: DAISY-CHAINABLE SENSORS AND STIMULATORS FOR IMPLANTATION IN LIVING TISSUE.

Figure 6:
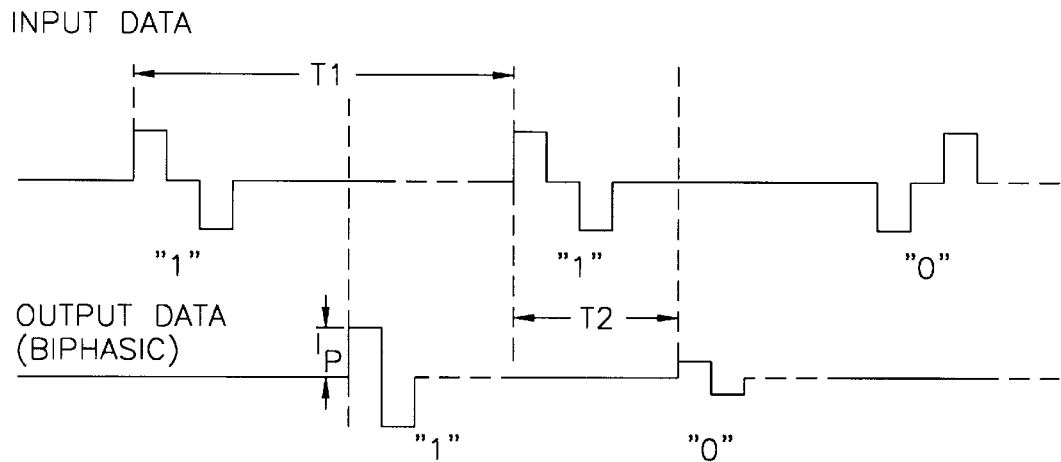
FIG. 6 is a timing diagram that illustrates input and output data sent to and received from an implantable sensor of the type shown in FIGS. 5A, 5B or 5C, and where the input data may also be used to provide operating power to the implantable sensor.

Turning back momentarily to FIG. 2, where a plurality of implantable, daisy-chainable sensors 18a, 18b . . . 18n are shown connected in tandem, a preferred manner of operation is for the controller 20 to provide operating power to, as well as to individually address and send data to and receive data from, each of the devices 18 that are connected thereto over the two-conductor bus made up of the conductors 14 and 16. One manner in which such powering and individual addressing is done is as shown in connection with FIGS. 6, 7 and 8. FIG. 6 illustrates, for example, a timing diagram that shows a preferred relationship between input data (top waveform) sent to the implantable devices and output data (bottom waveform) received from the implantable devices, as such data appears on the two LINE 1/LINE 2 conductors that connect all of the devices together. As seen in FIG. 6, the preferred form for the input data is biphasic pulses. Each biphasic pulses comprises a first current pulse of a first polarity, followed by a second current pulse of the same magnitude of the opposite polarity. Thus, the net current for each biphasic pulse is preferably zero, with the positive current pulse effectively balancing out the negative current pulse. The frequency of the pulse train shown in FIG. 6 (i.e., the inverse of the time period T1) is typically about 4000 pulses per second (pps), but may range from 10 pps to 500,000 pps. The typical widths of the current pulses are from 1 to 3 microseconds ($\mu$sec), with the magnitude of each current pulse typically ranging from 100 to 1000 microamps. A binary or logical "1" is represented by a biphasic pulse of one phase, e.g., a positive current pulse followed by a negative current pulse; while a binary or logical "0" is represented by a biphasic pulse of the opposite phase, e.g., a negative pulse followed by a positive pulse. Thus, as shown in FIG. 6, a binary "1" may be represented as a positive current pulse followed by a negative current pulse, while a binary "0" is represented by a negative current pulse followed by a positive current pulse.

As also seen in FIG. 6, the preferred form for the output data is also a biphasic pulse, amplitude modulated (or preferably ON/OFF modulated) as a function of whether the output data is a binary "1" or "0". In a preferred embodiment, the peak amplitude of the output data pulse for a binary "1" is $I_P$, while the peak amplitude of the output data pulse for a binary "0" is zero. Thus, in this preferred ON/OFF modulation scheme, the presence of an output data pulse represents a binary "1" and the absence of an output data pulse represents a binary "0". Output data pulses are inserted in the data stream appearing on the LINE 1/LINE 2 conductors pulses at a specified time T2 from the input data pulse so as to fall between the input data pulses, in a time-division multiplexed manner. Although the preferred form of the output data pulses is a biphasic pulse (to achieve current balancing), it is noted that in some instances a monophasic pulse at time T2 (and with amplitude of $I_P$ or zero) may be used.

Figure 7:
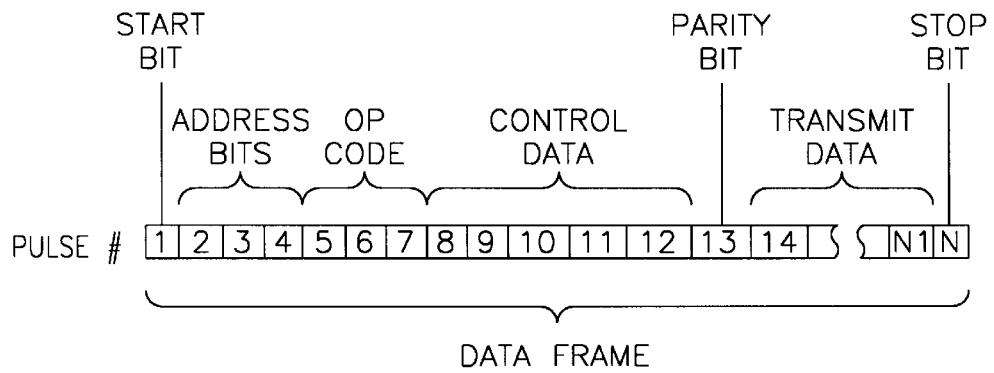
FIG. 7 illustrates a data frame used to communicate with the implantable sensor.
Figure 8:
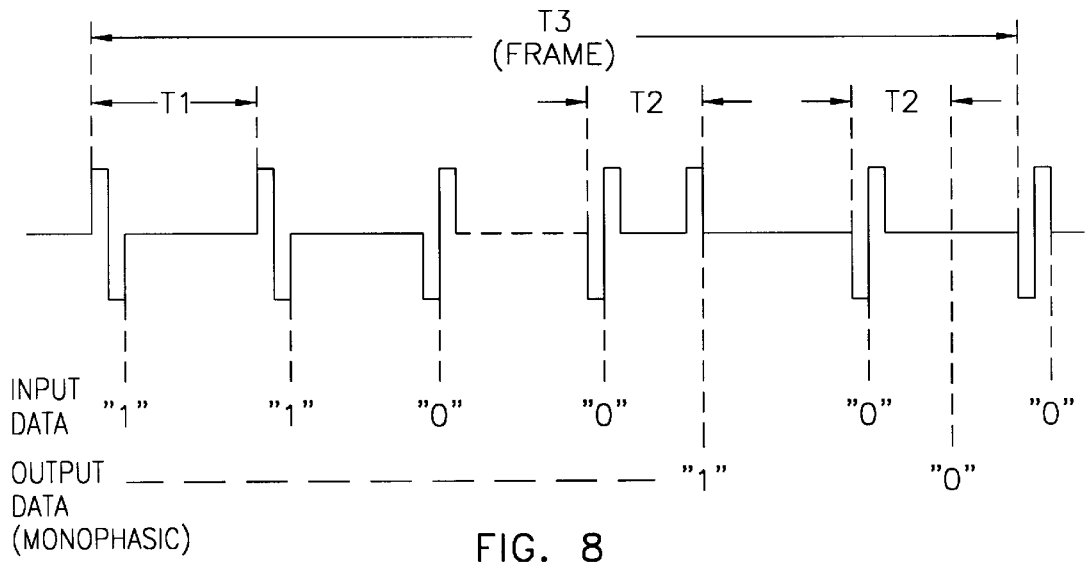
FIG. 8 is a timing diagram that illustrates time multiplexed input and output data within a data frame as it appears on the two-conductor bus connecting a plurality of daisy-chainable devices of the type shown in FIGS. 5A, 5B or 5C.

As shown in FIGS. 7 and 8, the input data and power sent over the LINE 1/LINE 2 conductors by the controller is divided into data frames of length T3. Within each data frame, N bits of data are found, where N is an integer typically ranging from 8 to 64. A representative assignment of the data bits included in the data frame is illustrated in FIG. 7.

Because the input data/power comprises biphasic pulses that occur at a regular interval or rate (e.g., every T1 seconds), the energy contained in such pulses may be utilized to provide the operating power for the circuits contained within the device 50". Such is accomplished using the rectifier circuit 60, 60' or 60" (FIGS. 5A, 5B or 5C), as detailed more fully below in conjunction with FIGS. 9–13.

The input and output data pulses of the type shown in FIGS. 6 and 8 are generated by the line interface circuit 62, 62' or 62" (FIGS. 5A, 5B or 5C). A schematic diagram of a preferred line interface circuit is described in the above-referenced copending patent application, Attorney Docket No. 56287 (see particularly FIG. 9 of the referenced application, and its accompanying text).

Low Power Rectifier Circuit

Figure 9:
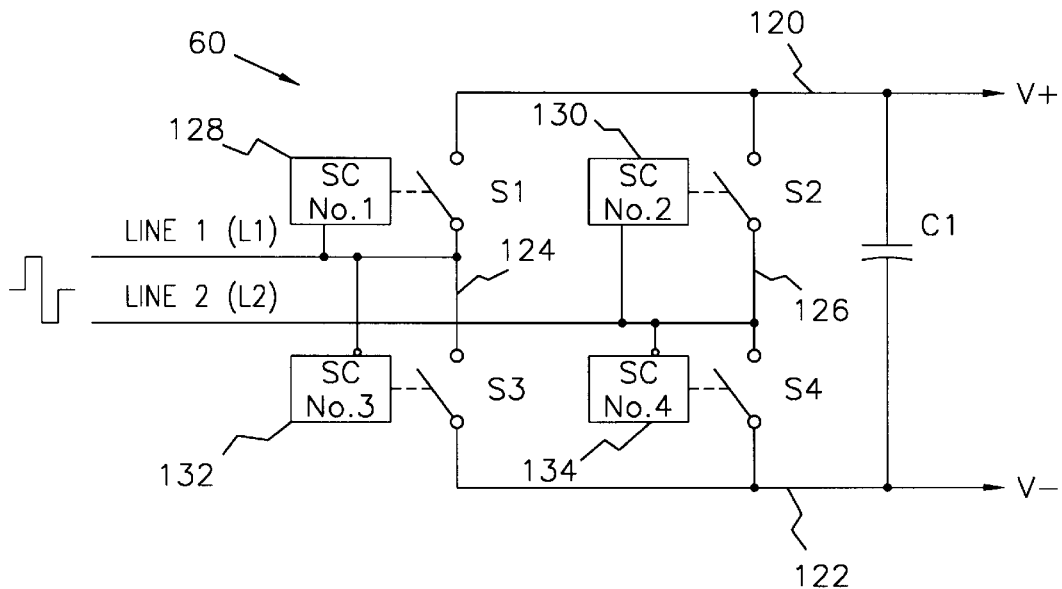
FIG. 9 shows a functional diagram of low power switching rectifier circuit made in accordance with the present invention.
Figures 10A, 10B:
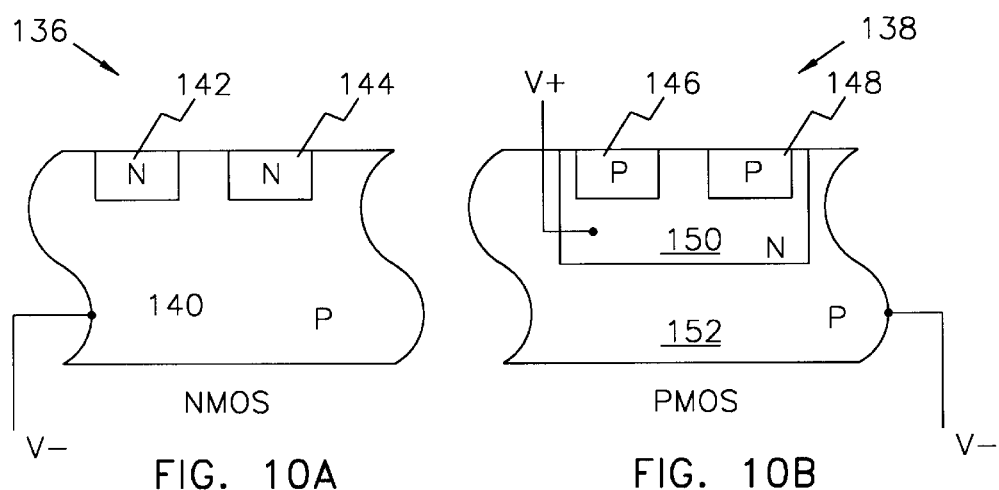
FIG. 10A illustrates the manner in which a parasitic diode is created in an N-MOS device.
FIG. 10B similarly illustrates the manner in which a parasitic PNP transistor is created in a P-MOS device.

Next, the low power rectifier circuit of the present invention will be described in conjunction with FIGS. 9–13. With reference to FIG. 9, a functional diagram of a low power rectifier circuit 60 is illustrated. As seen in FIG. 9, the rectifier circuit 60 functionally includes four switches S1, S2, S3 and S4. Switches S1 and S3 are connected in series, with a top terminal of switch S1 being connected to a V+ rail 120, and with a bottom terminal of switch S3 being connected to a V– rail 122 (where "top" and "bottom" refer to the orientation of the switches as shown in FIG. 9). The bottom terminal of switch S1 is connected to the top terminal of switch S3 to form a first input node 124 that is connected to the LINE 1 (L1) input signal line. In a similar manner, switches S2 and S4 are connected in series, with a top terminal of switch S2 being connected to the V+ rail 120, and with a bottom terminal of switch S4 being connected to the V– rail 122. The bottom terminal of switch S2 is connected to the top terminal of switch S4 to form a second input node 126 that is connected to the LINE 2 (L2) input signal line. A storage capacitor C1 is connected between the V+ rail 120 and the V– rail 122. The V+ rail and the V– rail thus provide the output terminals of the rectifier circuit.

Still with reference to FIG. 9, a first switch control circuit 128 controls operation (closing or opening) of switch S1. In a similar manner, a second switch control circuit 130 controls the operation of switch S2, a third switch control circuit 132 controls the operation of switch S3, and a fourth control circuit 134 controls the operation of switch S4. the control circuits 128 and 132 are coupled to LINE 1, while control circuits 130 and 134 are coupled to LINE 2. When any of the switches S1 through S4 is OFF, the switch is said to be "open", providing a very high impedance between its top and bottom terminals. Likewise, when any of the switches S1 through S4 is ON, the switch is said to be "closed", providing a very low impedance path between its top and bottom terminals. Control circuits 128 and 130 respond to a high input signal on LINE 1 or LINE 2 by closing their respective switches S1 or S2. Control circuits 132 and 134 respond to a low input signal on LINE 1 or LINE 2 by closing their respective switches S3 or S4.

In operation, it is thus seen that when a biphasic pulse is received over input signal lines LINE 1 and LINE 2, the first half or phase of the pulse causes LINE 1 to be positive relative to LINE 2. In effect, this means that during the first half of the biphasic pulse, LINE 1 is positive and LINE 2 is negative. In turn, this causes causes switch control circuit 128 to close switch S1, and switch control circuit 134 to close switch S4. Switches S2 and S3 remain open. With switches S1 and S4 closed, LINE 1 and LINE 2 are thus connected across capacitor C1, allowing the energy contained within the biphasic pulse to be stored on C1.

During the second half or phase of the biphasic pulse, LINE 1 becomes negative relative to LINE 2. This causes switches S3 and S2 to close, and switches S1 and S4 to open, which in effect connects capacitor C1 across LINE 2 and LINE 1, but with the opposite polarity of the previous connection. Because the second half or phase of the biphasic pulse is of the opposite polarity from the first half or phase, the charge associated with the opposite-polarity connection of switches S2 and S3 is additive to the charge obtained from the connection of switches S1 and S4. In this manner, it is seen that true full-wave rectification of the incoming biphasic pulse is obtained through automatic sequential closing of switches S1/S4 and S2/S3 in synchrony with the phases of the biphasic pulse.

The switches S1, S2, S3 and S4, as well as the switch control circuits 128, 130, 132, and 134 may be realized using any suitable switching and/or detecting devices. Of course, for implantable purposes, all the components are preferably realized using semiconductor components, e.g., low power CMOS FET devices (which includes both N-MOS and P-MOS FET transistors).

One problem associated with a switched rectifier circuit of the type shown in FIG. 9 is that in order for the switch control circuits 128, 130, 132 and 134 to operate, i.e., in order to be able to detect the phases of the biphasic pulse so that the switches S1, S2, S3 and S4 can be closed and opened in synchrony with such phases, there must be an operating voltage present that can power the control circuits. Such operating voltage is typically obtained from the V+ rail 120 and the V– rail 122, i.e., from the charge stored on storage capacitor C1. However, if a sufficiently long time has passed since the capacitor C1 was charged, then no charge of significance remains on capacitor C1, which means no operating voltage is present, and the switch control circuits 128, 130, 132, and 134 will not operate.

There exist various ways in which an initial start up charge could be placed on capacitor C1, thereby providing operating power to the control circuits, and enabling the rectifier circuit to perform its intended function. For example, a special monitoring circuit could detect when insufficient operating voltage was present on C1 and, if so, trigger a separate charge-up circuit that would accumulate sufficient charge from the incoming signal for storage on C1. Alternatively, a backup battery could be employed that is momentarily connected to capacitor C1, e.g., from a remote location, to charge C1 up whenever the charge thereon is insufficient to operate the control circuits.

However, the preferred way to start-up the rectifier circuit is to rely on parasitic diodes and transistors that are inherently present in the fabricated circuitry. To illustrate why such parasitic elements are present, reference is made to FIGS. 10A and 10B wherein a diagrammatic representation of an N-MOS FET 136 (FIG. 10A) and a P-MOS FET 138 (FIG. 10B) is shown. The N-MOS FET 136 includes a P-doped substrate 140 into which source and drain N-doped regions 142 and 144 are placed. (For simplicity, the gate structure associated with the FET devices shown in FIGS. 10A and 10B has been omitted.) The P-MOS FET 138 similarly includes P-doped source and drain regions 146 and 148 within an N-doped well region 150 of a P-doped substrate 152. A parasitic P-N diode is formed in the N-MOS device 136 of FIG. 10A by virtue of the P-doped substrate 140 being adjacent to the N-doped source and drain regions 142 and 144. In a similar manner, a parasitic PNP bipolar transistor is formed in the P-MOS device 138 of FIG. 10B by virtue of the P-substrate 152 being adjacent the N-well 150, which in turn is adjacent either the source or drain regions 146 or 148.

In most N-MOS or P-MOS devices, the existence of such parasitic elements as the PN diode in N-MOS device 136, or the PNP transistor in P-MOS device 138, is not an important factor because the device is biased in such a way that such parasitic elements are reversed biased, and hence not operable. However, the present invention advantageously takes advantage of the fact that such parasitic elements are present because it is such parasitic elements that allow initial rectification to occur in the absence of a supply voltage stored on capacitor C1.

To illustrate how such parasitic elements accomplish this initial rectification, reference is next made to FIG. 10 which shows a block/schematic diagram of a preferred embodiment of the low power rectifier circuit of the present invention. In FIG. 10, the four rectifying switches are realized using four FET transistors, M1, M2, M3 and M4. FET transistors M1 and M2 are P-MOS transistors, and transistors M3 and M4 are N-MOS transistors. (Note that in the figures of the present application, P-MOS transistors are identified by a diagonal line that connects the source terminal to the drain terminal; whereas N-MOS transistors are identified by the absence of such diagonal line.) Parasitic PNP transistors Q1 and Q2 are also shown in FIG. 10 (with phantom lines) as being shunted across P-MOS switches M1 and M2. More particularly, as shown in FIG. 10, the base terminals of Q1 and Q2 are connected together and to the V+ rail 120. The emitter terminal of Q1 is connected to LINE 1, and the emitter terminal of Q2 is connected to LINE 2. The collector terminals of both Q1 and Q2 are connected to the V– rail 122.

Parasitic PN diodes D1 and D2 are likewise shown in FIG. 10 (with phantom lines) as being shunted across N-MOS switches M3 and M4. More particularly, as seen in FIG. 10, the anode of both diode D1 and diode D2 is connected to the V– rail 122, while the cathode of diode D1 is connected to LINE 1, and the cathode of diode D2 is connected to LINE 2.

In operation, when an incoming biphasic (or other pulsed or ac) signal is first presented between LINE 1 and LINE 2 at a time when there is no supply voltage stored on capacitor C1, i.e., at a time when the supply voltage between the V+ rail 120 and the V– rail 122 is zero, the positive phase of such incoming signal forward biases the PN emitter-base junction of parasitic transistor Q1, allowing a portion, $1/\beta$ (where $\beta$ is the current gain of Q1), of the positive phase of the signal to pass through to the V+ rail 120 and onto capacitor C1 at the same time that the parasitic diode D1 is reversed biased and blocks this positive phase from passing through to the V– rail 122. At the same time that the positive phase is on LINE 1, LINE 2 is negative relative to LINE 1. With LINE 2 negative, the PN emitter-base junction of parasitic transistor Q2 is reversed biased, blocking any connection of LINE 2 to the V+ rail 120, but the parasitic diode D2 is forward biased, allowing LINE 2 to be connected through diode D2 to the V– rail 122.

In a similar manner, the negative phase of the incoming signal (which makes LINE 1 negative relative to LINE 2) forward biases the parasitic diode D1, connecting LINE 2 to the V– rail 122, and forward biases the emitter-base junction of parasitic transistor Q2, connecting LINE 2 to the V+ rail 120. At this same time (during the negative phase of the incoming signal), the emitter-base junction of Q1 is reversed biased, blocking any connection between LINE 1 and the V+ rail 120, and diode D2 is reversed biased, blocking any connection between LINE 2 and the V− rail 122.

Thus, it is seen that the parasitic elements Q1, Q2, D1 and D2 actually function as a full wave rectifier circuit, albeit a somewhat inefficient rectifier circuit (the voltage drop across the PN junctions is typically about 0.7 volts, and a significant portion of the pnp emitter current is lost to V− as collector current), even in the absence of an operating voltage on the V+ and V− rails. In this regard, it is helpful if the overall PFET design minimizes the value of β of the parasitic transistors, thereby making the operation of this inefficient rectifier circuit somewhat more efficient than it might otherwise be.

After a few cycles of inefficient rectification by the parasitic elements, sufficient charge is stored on capacitor C1 to provide an operating voltage between the V+ and V− voltage supply rails 120 and 122. Once a supply voltage is present, the switch control circuits 128, 130, 132 and 134, as well as the switches M1, M2, M3 and M4, are able to operate to perform their intended, highly efficient, rectifying function.

Figure 11:
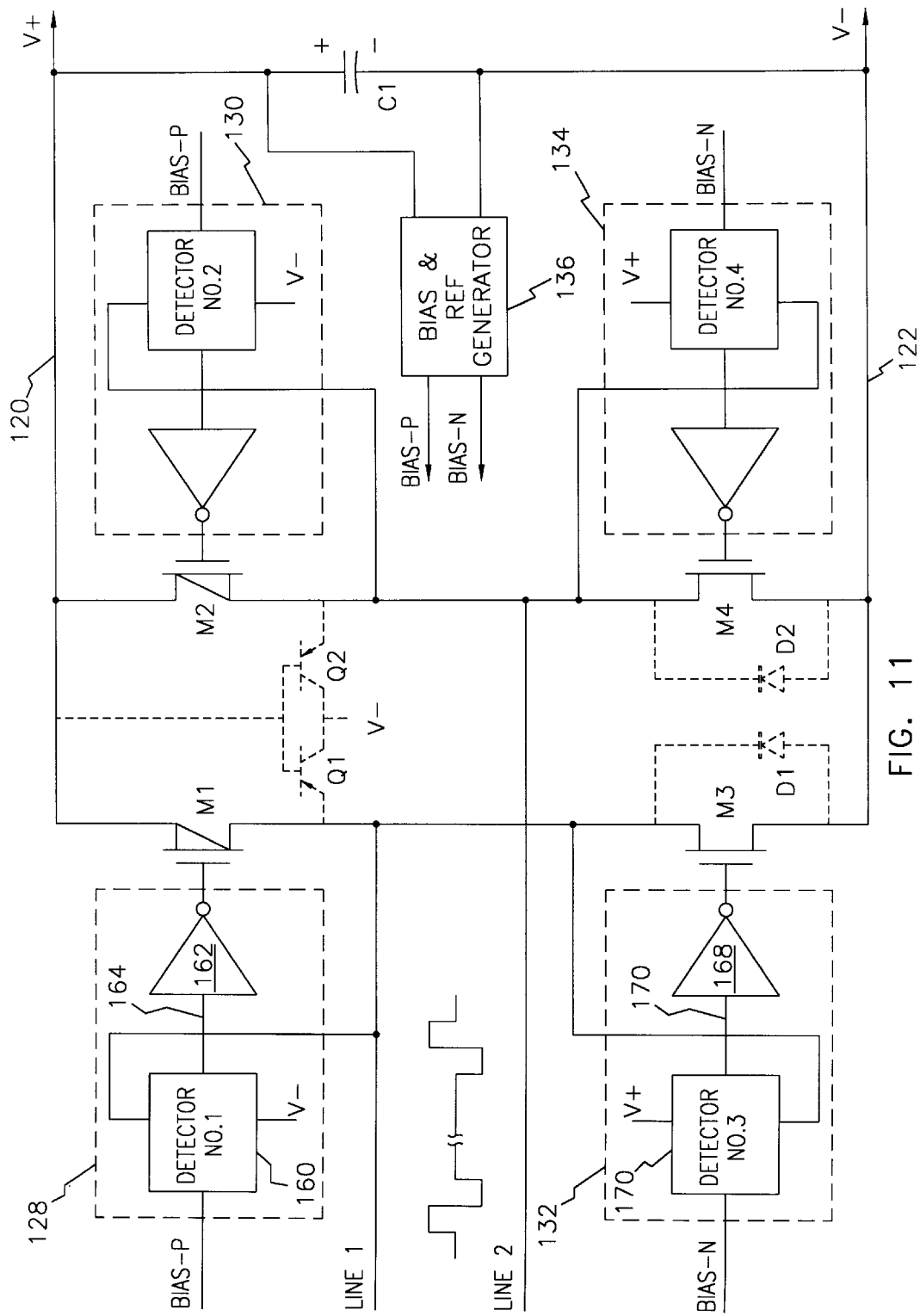
FIG. 11 is a block diagram of a low power rectifier circuit made in accordance with the present invention, showing the use of two P-MOS switches and two N-MOS switches, along with the accompanying parasitic diodes and transistors that are inherent in such switches.

As seen in FIG. 11, the switch control circuit 128 is made up of a detector circuit 160 and an inverter circuit 162. The detector circuit 160 is biased ON only when the signal on LINE 1 exceeds a BIAS-P reference voltage by about one threshold. When biased OFF, the output of detector 160, on signal line 164, remains low, which low becomes a high at the output of inverter 162. This high is applied to the gate of P-MOS switch M1, keeping M1 OFF. (Note, as used herein, the terms "high" and "low" refer to the voltage present on a given signal line relative to the voltage supply rails V+ and V−, where the V+ rail is (when a supply voltage is present) maintained "high" and the V− rail is maintained "low".) When the detector 160 is biased ON, its output, on signal line 164, goes high. This high signal becomes a low signal at the output of inverter circuit 162, forcing the gate of P-MOS switch M1 low, which turns M1 ON, thereby effectively connecting LINE 1 to the V+ rail 120.

As further seen in FIG. 11, the switch control circuit 132, which controls the N-MOS switch M3, is similarly made up of a detector circuit 166 and an inverter circuit 170. The detector circuit 166 is biased ON only when a negative signal on LINE 1 is more negative than a BIAS-N reference voltage by about one threshold. At all other times, the detector circuit 166 is biased OFF. When biased OFF, the output of detector 160, on signal line 170, is high, which high becomes a low at the output of inverter 168. This low is applied to the gate of N-MOS switch M3, keeping M3 OFF. When biased ON, the output of the detector 166, on signal line 170, goes low. This low signal is converted to a high signal at the output of inverter circuit 168, forcing the gate of N-MOS switch M3 high, which turns M3 ON, thereby effectively connecting LINE 1 to the V− rail 122.

It should be noted that the switch control circuits 128 and 132 could be combined into a single control circuit, if desired, with P-MOS switch M1 being turned ON whenever a voltage pulse on LINE 1 is sufficiently positive relative to LINE 2; and with N-MOS switch M3 being turned ON whenever a voltage pulse on LINE 1 is sufficiently negative relative to LINE 2.

The operation of switch control circuit 130, which controls P-MOS switch M2, parallels that of switch control circuit 128, described above, except that the incoming signal is on LINE 2, rather than LINE 1. Likewise, the operation of switch control circuit 134, which controls N-MOS switch M4, parallels that of switch control circuit 132, described above, except that the incoming signal is on LINE 2, rather than LINE 1.

The two switch control circuits 130 and 134 could be combined into a single control circuit, if desired, with P-MOS switch M2 being turned ON whenever a voltage pulse on LINE 2 is sufficiently positive relative to LINE 1; and with N-MOS switch M4 being turned ON whenever a voltage pulse on LINE 2 is sufficiently negative relative to LINE 1.

A Bias and Reference Generator circuit 136 generates the reference voltages BIAS-P and BIAS-N. While these reference voltages may be any value that permits the easy detection of low and high signals on LINE 1 and LINE 2, in the preferred embodiment, discussed below in connection with FIGS. 12A, 12B and 13, the BIAS-P reference is maintained at a voltage that is equal to the voltage on the V+ rail 120 less about one FET threshold voltage (approximately 0.9 volts). Similarly, the BIAS-N reference is maintained at a voltage that is about one FETF threshold voltage above the voltage on the V− rail 122. Thus, if the V+ rail 120 is maintained at, e.g., 3.5 volts, and the V− rail 122 is maintained at zero volts (ground), then the BIAS-P reference would be about 3.5−0.9=2.6 volts, and the BIAS-N reference would be about 0+0.9=0.9 volts. These V+ and V− and BIAS-P and BIAS-N values, of course, are only exemplary, not limiting.

Figure 12A:
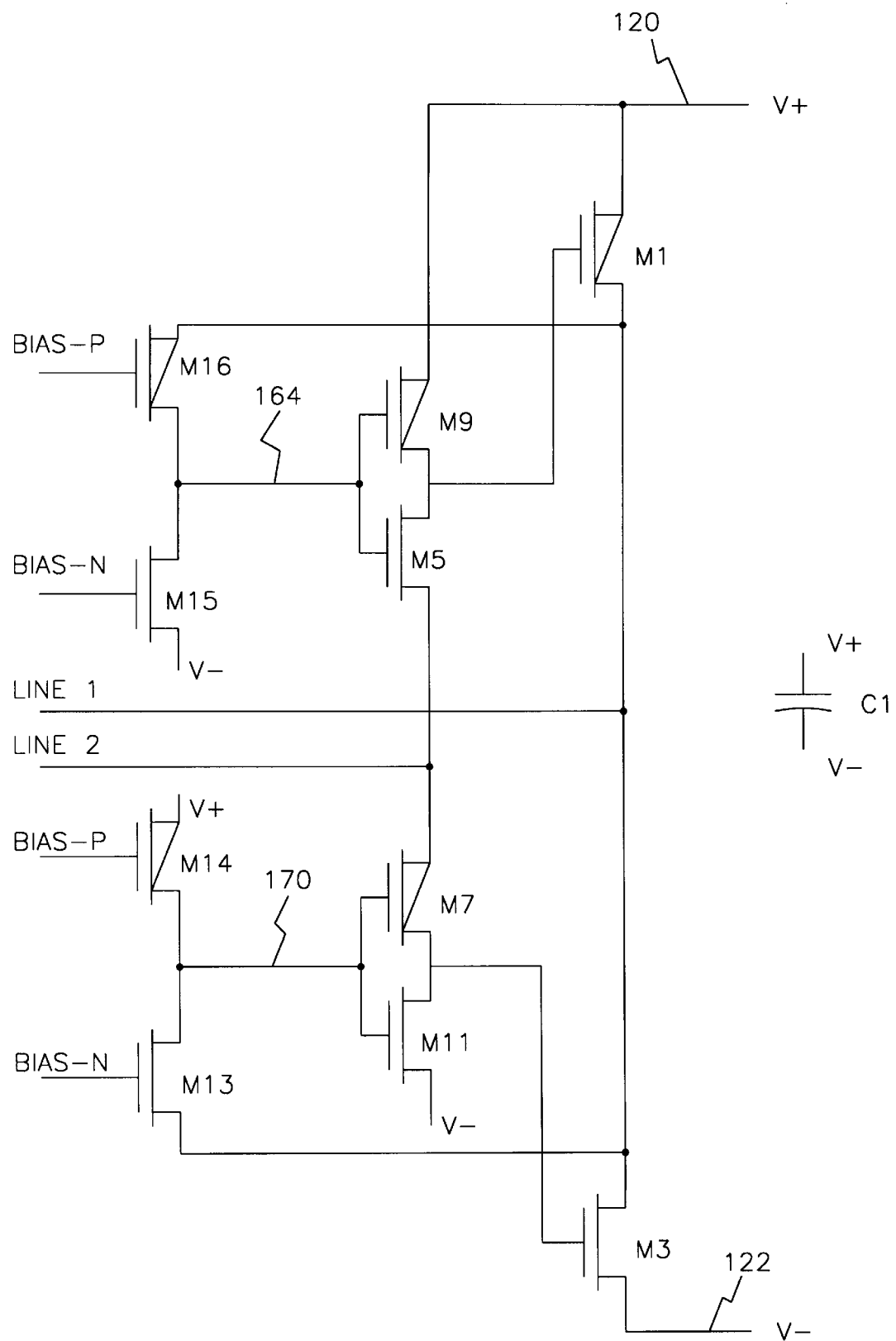
FIGS. 12A and 12B show a schematic diagram of a preferred embodiment of the Switches, Inverters and Detectors of the low power rectifier circuit of FIG. 11.
Figure 12B:
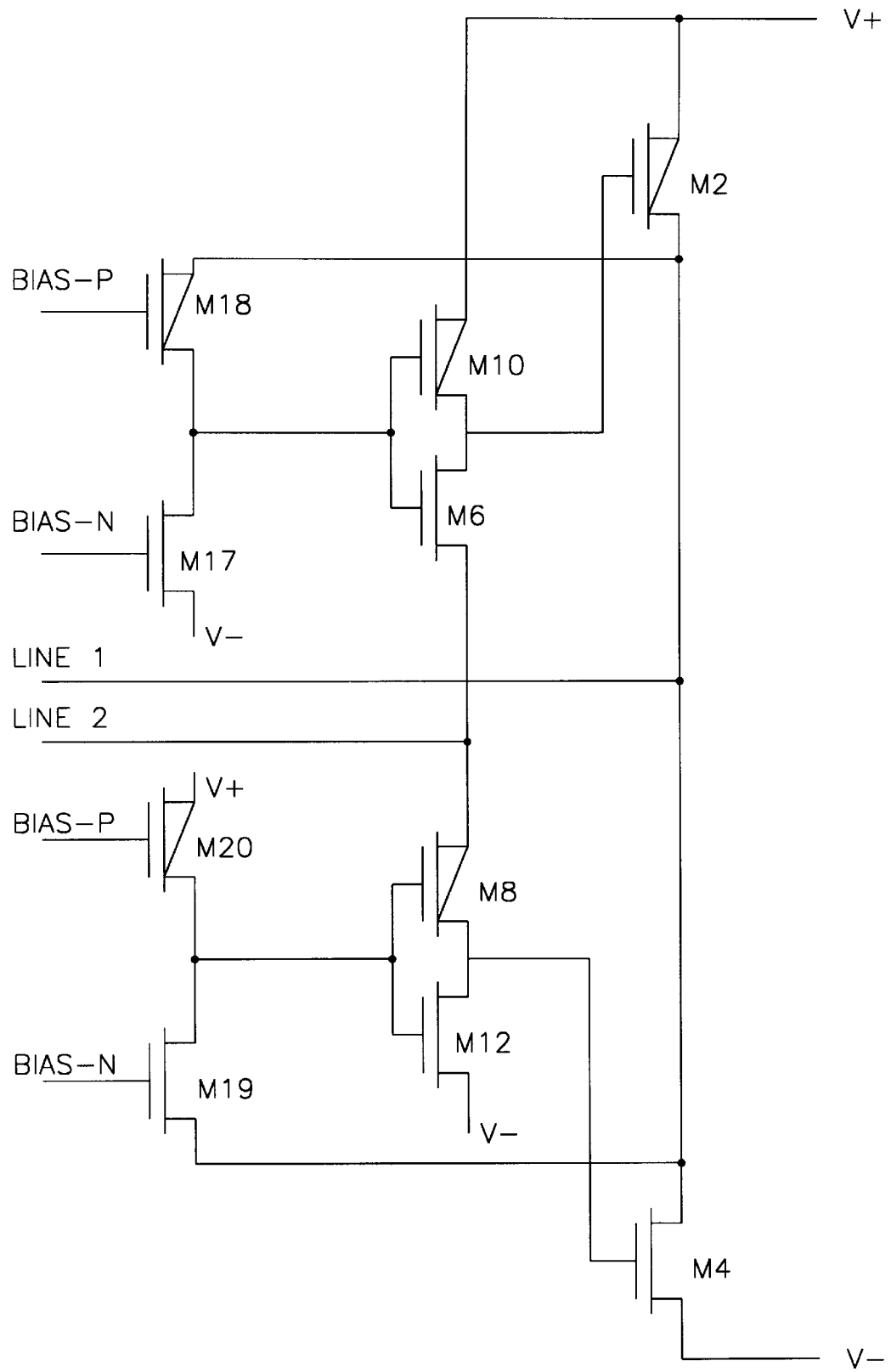
Figure 13:
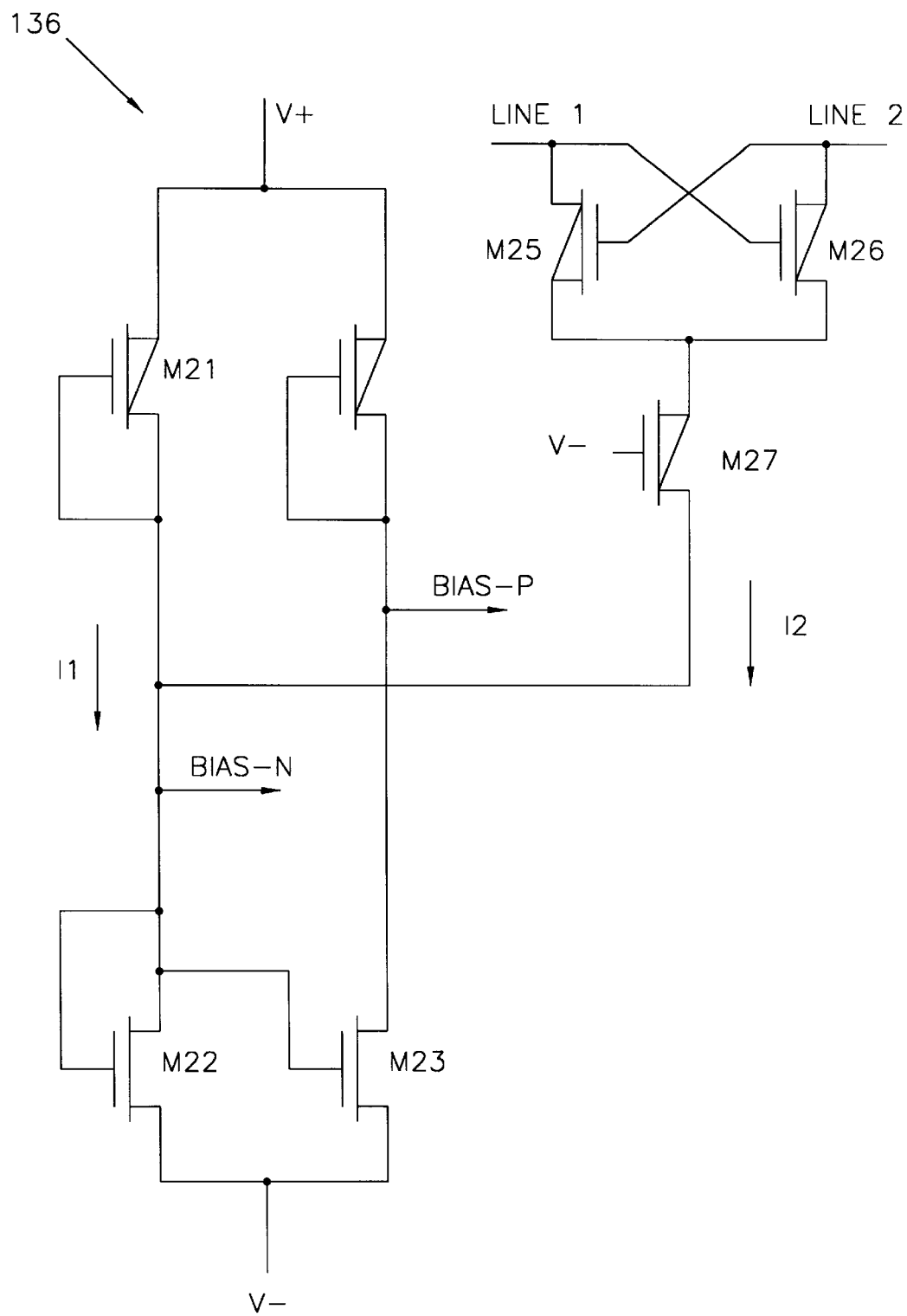
FIG. 13 is a schematic diagram of the Bias and Reference Generator of FIG. 11.

The preferred implementation of the low power rectifier circuit shown in FIG. 11 is realized using N-MOS and P-MOS transistors for the four detector circuits, four inverter circuits, and bias and reference generator 136, as well as for the switches M1, M2, M3 and M4, as shown in the schematic diagrams of FIGS. 12A, 12B and 13. FIG. 12A shows the switches M1 and M2 along with their corresponding inverter circuits and detector circuits. FIG. 12B shows the switches M3 and M4 along with their corresponding inverter circuits and detector circuits. FIG. 13 shows the bias and reference generator circuit 136.

When FIG. 12A, 12B and 13 are considered together, it is seen that the low power rectifier circuit of the present invention includes four separate rectifying circuits, each associated with one of the switches M1, M2, M3 or M4, having similar topology which do the rectification, along with a biasing circuit. During an input pulse on LINE 1 and LINE 2, two of the rectifying circuits are activated (turned ON) in the manner of a bridge rectifier, and two of the rectifying circuits are turned OFF. Which two switches are turned ON and which two are turned OFF depends upon the polarity of the incoming pulse. For a biphasic pulse (having both positive and negative phases), a sequence of: (1) two switches ON and two OFF, followed by (2) the two switches that were OFF being ON, and the two switches that were ON being OFF, occurs, as described previously. Because the operation and topology of each rectifying circuit is similar, only the operation of two of the rectifier circuits will be presented (the two shown in FIG. 12A). The operation of the two rectifier circuits shown in FIG. 12B is identical to the operation of the two described in FIG. 12A, except for the reversal of LINE 1 and LINE 2.

In FIG. 12A, P-MOS field effect transistor FETF) M16 and N-MOS FET M15 form the detector circuit 160 (shown in FIG. 11), and P-MOS FET M9 and N-MOS FET M5 form the inverter circuit 162 (also shown in FIG. 11). Rectifier FET switch M1 is driven from the M5/M9 inverter, whose input (on signal line 164) comes from the M15/M16 detector circuit. When turned ON, switch M1 (as well as the other switches M2, M3 and M4) exhibits a very low drain-to-source voltage, e.g., 50 mV. The M15/M16 detector has two separate inputs. The N-MOS FET M15 has the bias signal BIAS-N as its input (applied to its gate terminal), and the P-MOS FET M16 has the bias signal BIAS-P as its input. If the M15/M16 FETs were connected to the V+ and V− lines 120 and 122, these bias voltage applied to the respective gate terminals would cause each transistor M15 and M16 to draw a certain current. However, M16 is not connected simply to the V+ and V− lines. Rather, P-MOS M16 is connected directly to the LINE 1 input line, which is the same line the rectifying switch M1 is connected to. This means that in the absence of a positive pulse on LINE 1, the M15/M16 detector is biased OFF because the LINE 1 voltage will be somewhere between V+ and V−, which means P-MOS FET M16 will be turned off (because its gate to source voltage is reversed). During this time (in the absence of a positive pulse on LINE 1), the N-MOS FET M15 is ON (its gate-to-source voltage being the BIAS-N voltage applied to the gate), which forces signal line 164 low. This low drives the M5/M9 inverter so that its output, applied to the gate of main switch M1, is high, keeping M1 OFF.

When a positive pulse comes along on LINE 1 which exceeds V+ (which will usually be the case), the gate-to-source voltage of P-MOS FET M16 biases M16 ON. The FET M16 is fabricated as a wider FET than N-MOS FET M15 (see Table 1, below, for the dimensions of the various FETs used in FIGS. 12A, 12B and 13), so M16 draws more current and reverses the voltage on the input of the M5/M9 inverter (signal line 164). This reversal, in turn, pulls the gate of P-MOS FET switch M1 low, which turns M1 ON, thereby connecting LINE 1 to the V+ line or rail 120. While ON, the rectifier switch M1 conducts current from LINE 1 to the V+ line, thereby charging capacitor C1. As soon as the input pulse on LINE 1 decays to the point where the input pulse is no longer greater than one threshold greater than BIAS-P, the P-MOS FET M16 turns OFF, and the M16/M15 detector is thus biased OFF, pulling line 164 low, which (through the M5/M9 inverter) causes the gate of FET M1 to go high, turning P-MOS FET M1 OFF. Note that one leg of the M5/M9 inverter stage, i.e., the source of N-MOS FET M5, is connected to LINE 2, rather than to V−. This connection helps on startup and increases the turn on drive to the rectifier FET M1.

Still referring to FIG. 12A, P-MOS FET M14 and N-MOS FET M13 form the detector circuit 166 (shown in FIG. 11), and P-MOS M7 and N-MOS FET M11 form the inverter circuit 168 (also shown in FIG. 11). Rectifier FET switch M3 is driven from the M7/M11 inverter, whose input (on signal line 170) comes from the M13/M14 detector circuit. The M13/M14 detector has two separate inputs. The N-MOS FET M13 has the bias signal BIAS-N as its input (applied to its gate terminal), and the P-MOS FET M14 has the bias signal BIAS-P as its input. N-MOS FET M13 is connected directly to the LINE 1 input line, which is the same line the rectifying switch M3 is connected to. This means that in the absence of a negative pulse on LINE 1, the M14/M15 detector is biased OFF because the LINE 1 voltage will be somewhere between V+ and V−, which means N-MOS FET M13 will be turned off (because its gate to source voltage is reversed). During this time (in the absence of a negative pulse on LINE 1), the P-MOS FET M14 is ON (its gate-to-source voltage being biased by the BIAS-P voltage applied to the gate and the V+ voltage applied to its source), which forces signal line 170 high. This high drives the M7/M11 inverter so that its output, applied to the gate of main FET switch M3, is low, keeping M3 OFF.

When a negative pulse comes along on LINE 1 (i.e., the negative half of a biphasic pulse) which exceeds V− in amplitude (which will usually be the case), the gate-to-source voltage of N-MOS FET M13 reaches threshold, thereby biasing N-MOS FET M13 ON. The FET M13 is fabricated as a wider FET than P-MOS FET M14 (see Table 1), so M13 draws more current and reverses the voltage on the input of the M7/M11 inverter (signal line 170). This reversal, in turn, pulls the gate of N-MOS FET switch M3 high, which turns M3 ON, thereby connecting LINE 1 to the V− line or rail 122. While ON, the rectifier switch M3 then conducts current from LINE 1 to the V− line, thereby further charging capacitor C1. As soon as the negative input pulse on LINE 1 decays to the point where the input pulse is no longer greater than one diode drop below BIAS-N, the N-MOS FET M13 turns OFF, and the M13/M14 detector is thus biased OFF, forcing line 170 high, which (through the M7/M11 inverter) causes the gate of FET M3 to go low, turning N-MOS FET M3 OFF. As shown in FIG. 12A, one leg of the M7/M11 inverter stage, i.e., the source of P-MOS FET M7, is connected to LINE 2, rather than to V+. This connection helps on startup and increases the turn on drive to the rectifier FET M3.

FIG. 12B shows the detector and inverter circuitry for driving rectifier FET switches M3 and M4. In all respects, the topology and operation of such circuitry is the same as that described above in connection with FIG. 12A, except that LINE 1 and LINE 2 are reversed.

Turning next to FIG. 13, a preferred bias and reference generator circuit 136 is shown. Such circuit 136 includes seven FETs, M21–M27. A long P-MOS FET M21 is used as a current limiting resistor to feed a diode-connected N-MOS FET M22, which provides the bias voltage BIAS-N. The bias or reference voltage BIAS-N is thus about one threshold voltage greater than the voltage on the V− line 122.

The current I1 that flows through M21 is referred to as a static bias current because it is present at all times that the low power rectifier circuit is powered on, i.e., at all times whenever an operating voltage is present on the V+ and V− lines or rails. A typical value for the static bias current I1 is about 0.2 μa.

Still with reference to FIG. 13, it is seen that the diode-connected N-MOS FET M22 drives another N-MOS FET M23. This FET M23 mirrors the static bias current I1 to another diode-connected P-MOS FET M24, which provides the bias voltage BIAS-P. Thus, it is seen that the bias or reference voltage BIAS-P is one threshold voltage less than the voltage on the V+ line 120.

As further seen in FIG. 13, two P-MOS FETs M25 and M26 are cross connected to LINE 1 and LINE 2 so that the more positive one is turned ON whenever a biphasic pulse is present on LINE 1/LINE 2. That is, during the positive phase of a biphasic pulse, M25 is turned ON; and during the negative phase of a biphasic pulse, M26 is turned ON. Current from the LINE 1/LINE 2 connected FETs M25/M26 goes through another P-FET M27, which is always biased ON, and which is used to limit the current flowing through M25/M26 and M27 to a value I2.

The current I2 is referred to as a dynamic bias current, and it typically has a value about 100 times that of I1, i.e., about 20 μa. However, note that I2 is only allowed to flow during the time that an input pulse is present on LINE 1/LINE 2, which (from a duty cycle point-of-view) is a relatively short time, e.g., only 4 μsec out of 240 μsec. When the dynamic bias current I2 is flowing, the current flowing through diode-connected M22 and diode-connected M24 is also increased, thereby causing the bias/reference voltages BIAS-N and BIAS-P to be adjusted appropriately (increasing both slightly).

The static bias current I1 thus functions as a background or stand-by bias current that keeps everything working properly during the time between pulses on the input signal lines LINE 1 and LINE 2, i.e., during those times when there is little if any voltage difference between LINE 1 and LINE 2. When an input pulse arrives, i.e., during those times when there is a large voltage difference between LINE 1 and LINE 2, the dynamic bias current kicks in, providing an operational mode during which the bias current and resulting BIAS-P and BIAS-N reference voltages are set to a value better suited for the time when the input pulse is present. The increase of the BIAS-P and BIAS-N reference voltages during the operational mode provides higher currents for quickly driving the appropriate detector circuits ON or OFF so that the corresponding rectifier switches M1–M4 can quickly switch ON or OFF, thereby providing the desired rectification function. Because the larger dynamic bias current I2 is only present during the operational mode, which is a relatively short period of time, the overall power consumption of the rectifier circuit is kept low.

Table 1 below characterizes the various P-MOS and N-MOS transistors shown in the schematic diagram of FIGS. 12A, 12B and 13 by size, and further includes a preferred value of the storage capacitor C1. The type of characterization (by dimension or size) of the various N-MOS and P-MOS FET transistors used within an IC is known and understood by those of skill in the semiconductor processing art. Advantageously, by selectively controlling the size (dimensions) of such transistors during the IC processing steps, the performance of the N-MOS or P-MOS transistors can be controlled or tailored for the specific design for which the transistor is used. Thus a relatively "long" N-FET, having a size of, e.g., 5/10, where the first number represents the width and the second number represents the length, may exhibit a higher turn-on resistance (and hence a slower turn on time) than would, e.g., a relatively "wide" and "short" N-FET, having a size of 40/2. In general, the wider the FET, the more current carrying capacity it has; and the longer the FET, the more resistance it will exhibit.

TABLE 1

Transistor Sizes and Component Values for FIGS. 12A, 12B and 13

| Transistor or Component Ref. | Type | Dimensions/Size (W/L in microns) |
|---|---|---|
| M1 | P-MOS | 100/0.8 |
| M2 | P-MOS | 100/0.8 |
| M3 | N-MOS | 50/0.80 |
| M4 | N-MOS | 50/0.80 |
| M5 | N-MOS | 2.8/4.0 |
| M6 | N-MOS | 2.8/4.0 |
| M7 | P-MOS | 2.8/4.0 |
| M8 | P-MOS | 2.8/4.0 |
| M9 | P-MOS | 2.8/4.0 |
| M10 | P-MOS | 2.8/4.0 |
| M11 | N-MOS | 2.8/4.0 |
| M12 | N-MOS | 2.8/4.0 |
| M13 | N-MOS | 5.0/2.0 |
| M14 | N-MOS | 4.0/2.0 |
| M15 | N-MOS | 4.0/2.0 |
| M16 | P-MOS | 5.0/2.0 |
| M17 | N-MOS | 4.0/2.0 |
| M18 | P-MOS | 5.0/2.0 |
| M19 | N-MOS | 5.0/2.0 |
| M20 | P-MOS | 4.0/2.0 |
| M21 | P-MOS | 2.4/2000 |
| M22 | N-MOS | 4.0/2.0 |
| M23 | N-MOS | 4.0/2.0 |
| M24 | P-MOS | 5.0/2.0 |
| M25 | P-MOS | 4.8/0.8 |
| M26 | P-MOS | 4.8/0.8 |
| M27 | P-MOS | 2.0/50 |
| C1 | capacitor | 0.033 $\mu$F |

As described above, it is thus seen that the present invention provides a very low power rectifier circuit, particularly suited for use within an implantable device, such as an implantable sensor, that exhibits a very low turn on voltage and that is self-starting, i.e., that responds to an incoming ac signal, such as a pulse train of biphasic pulses, even when no operating voltage is currently present.

It is further seen that the invention provides such a low power rectifier circuit that self-generates all the necessary control signals needed to turn the rectifying switches ON and OFF at the appropriate time as a function of the incoming ac signal. More particularly, it is seen that circuit operates using a very low static bias current for most of the time when the rectifier circuit is operating in a stand-by mode, but which automatically triggers a larger dynamic bias current during those times when an incoming pulse to be rectified is present.

While the invention herein disclosed has been described by means of specific embodiments and applications thereof, numerous modifications and variations could be made thereto by those skilled in the art without departing from the scope of the invention set forth in the claims.

What is claimed is:

1. A low power switched rectifier circuit comprising:
    first and second voltage rails (120, 122);
    a storage capacitor (C1) connected between the first and second voltage rails;
    first and second input lines (LINE 1, LINE 2);
    a first switch (M1) connecting the first input line to the first voltage rail;
    a second switch (M2) connecting the second input line to the first voltage rail;
    a third switch (M3) connecting the first input line to the second voltage rail;
    a fourth switch (M4) connecting the second input line to the second voltage rail;
    a detector circuit for each of said first, second, third, and fourth switches, respectively, powered by voltage on the storage capacitor, that automatically controls its respective switch to close and open as a function of the voltage signal appearing on the first input line relative to the second input line such that, in concert, the first and fourth switches close and the second and third switches open in response to a positive signal on the first input line relative to the second input line, and such that second and third switches close and the first and fourth switches open in response to a negative signal on the first input line relative to the second input line, whereby the first input line is automatically connected to the first voltage rail and the second input line is automatically connected to the second voltage rail whenever a positive signal appears on the first input line relative to the second input line, and whereby the first input line is automatically connected to the second voltage rail and the second input line is automatically connected to the first voltage rail whenever a negative signal appears on the first input line relative to the second input line; and startup means for supplying the storage capacitor with an initial voltage sufficient to power each of the detector circuits;

said low power switched rectifier circuit wherein all of said first, second, third, and fourth switches and respective detector circuits are all part of a single integrated circuit.

2. The low power switched rectifier circuit of claim 1 wherein the first, second, third and fourth switches and respective detector circuits comprise N-MOS and P-MOS complimentary field-effect transistors.

3. The low power switched rectifier circuit of claim 2 wherein the startup means comprises parasitic P-N junctions present in the N-MOS and P-MOS complimentary field-effect transistors.

4. The low power switched rectifier circuit of claim 2 wherein said single integrated circuit further includes a bias generator circuit that generates a plurality of bias signals used by the respective detector circuits to detect the presence of an incoming voltage signal on the first and second input signal lines.

5. The low power switched rectifier circuit of claim 4 wherein the bias generator circuit generates a first bias signal that is a fixed amount less than the voltage present on the storage capacitor as sensed on the first voltage rail, and wherein the first detector circuit closes the first switch to connect the first input line to the first voltage rail only when the incoming voltage signal on the first input line exceeds the first bias signal.

6. The low power switched rectifier circuit of claim 4 wherein the bias generator circuit generates a first bias signal that is a fixed amount less than the voltage present on the storage capacitor as sensed on the first voltage rail, and wherein the first detector circuit closes the first switch to connect the second input line to the first voltage rail only when the incoming voltage signal on the second input line exceeds the first bias signal.

7. The low power switched rectifier circuit of claim 6 wherein the bias generator circuit includes means for dynamically changing the first bias signal from a first value to a second value whenever an incoming voltage signal is present on the first input line relative to the second input line.

8. The low power switched rectifier circuit of claim 4 wherein the bias generator circuit generates a second bias signal that is a fixed amount smaller than a negative voltage present on the storage capacitor as sensed at the second voltage rail relative to the first voltage rail, and wherein the third detector circuit closes the third switch to connect the first input line to the second voltage rail only when the incoming voltage signal on the first input line relative to the second voltage line is a negative voltage greater than the second bias signal.

9. The low power switched rectifier circuit of claim 4 wherein the bias generator circuit generates a second bias signal that is a fixed amount smaller than a negative voltage present on the storage capacitor as sensed at the second voltage rail relative to the first voltage rail, and wherein the third detector circuit closes the third switch to connect the second input line to the second voltage rail only when the incoming voltage signal on the second input line relative to the second voltage line is a negative voltage greater than the second bias signal.

10. The low power switched rectifier circuit of claim 9 wherein the bias generator circuit includes means for dynamically changing the second bias signal from a first value to a second value whenever an incoming voltage signal is present on the second input line relative to the first input line.

11. An implantable device comprising;

an hermetically sealed case;

means for coupling power signals into said hermetically sealed case;

a rectifier circuit for rectifying the incoming power signals and generating an operating voltage therefrom; and electronic circuits within said hermetically sealed case and powered by said operating voltage for performing specified functions;

said rectifier circuit including a pair of input lines on which the power signal is received, a pair of output lines on which the operating voltage is made available, N-MOS and P-MOS field effect transistors (FET'S) for automatically connecting an appropriate one of the pair of input lines to an appropriate one of the pair of output lines in synchrony with positive and negative amplitude variations of the power signals, and a filter capacitor connected between the pair of output lines;

wherein N-MOS and P-MOS switches further comprise:

a first P-MOS FET (M1) that, when turned on, connects a first one of the input lines (LINE 1) to a first one of the output lines (V+);

a second P-MOS FET (M2) that, when turned on, connects a second one of the input lines (LINE 2) to the first one of the output lines (V+);

a first N-MOS FET (M3) that, when turned on, connects the first one of the input lines (LINE 1) to a second one of the output lines (V−);

a second N-MOS FET (M4) that, when turned on, connects the second one of the input lines (LINE 2) to the second one of the output lines (V−);

a first detector circuit that turns the first P-MOS FET switch (M1) on only when the power signal on LINE 1 relative to LINE 2 has a positive amplitude exceeding a first threshold value;

a second detector circuit that turns the second P-MOS FET switch (M2) on only when the power signal on LINE 2 relative to LINE 1 has a positive amplitude exceeding the first threshold value;

a third detector circuit that turns the first N-MOS FET switch (M3) on only when the power signal on LINE 1 relative to LINE 2 has a negative amplitude exceeding a second threshold value; and a fourth detector circuit that turns the second N-MOS FET switch (M4) on only when the power signal on LINE 2 relative to LINE 1 has a negative amplitude exceeding the second threshold value;

said implantable device wherein each of the first, second, third, and fourth detector circuits further comprise a complementary N-MOS and P-MOS transistor pair connected as a detector circuit to be biased ON only when a power signal greater than a bias reference voltage is present on the pair of input lines.

12. The implantable device of claim 11 wherein the complementary N-MOS and P-MOS transistor pair of each detector circuit has a first bias reference voltage connected to a gate terminal of its P-MOS transistor, and a second bias reference voltage connected to a gate terminal of its N-MOS transistor.

13. The implantable device of claim 12 further including a bias generator circuit that generates the first and second reference voltages, and wherein the bias generator circuit includes means for dynamically setting the first and second reference voltages to an operational level when a power signal is present on the pair of input lines, and to a low power stand-by level when a power signal is not present on the pair of input lines.

14. The implantable device of claim 11 further including a complementary N-MOS and P-MOS inverter circuit interposed between each detector circuit and the respective first/second P-MOS/N-MOS FET switch controlled by the detector circuit.

15. An implantable medical device comprising:
an hermetically sealed case;
means for coupling power signals into said hermetically sealed case;
a rectifier circuit for rectifying the incoming power signals and generating an operating voltage therefrom; and
electronic circuits within said hermetically sealed case and powered by said operating voltage for performing specified functions;
said rectifier circuit including a pair of input lines on which the power signal is received,
a pair of output lines on which the operating voltage is made available,
N-MOS and P-MOS field effect transistors (FET'S) for automatically connecting an appropriate one of the pair of input lines to an appropriate one of the pair of output lines in synchrony with positive and negative amplitude variations of the power signals, and
a filter capacitor connected between the pair of output lines;
said implantable device further including startup means for providing a voltage to the filter capacitor connected between the pair of output lines at a time when no operating voltage is present on said filter capacitor.

16. The implantable device of claim 15 wherein the startup means comprises parasitic diodes within the N-MOS FET switches, and parasitic PNP bipolar transistors within the P-MOS FET switches, which parasitic diodes and transistors are sufficiently forward biased by an initial power signal on the pair of input lines to cause an initial operating voltage derived from the initial power signal to be stored on said filter capacitor.

17. A low power rectifier circuit comprising:
means for receiving a pulsed power signal;
a pair of input lines on which the pulsed power signal is received;
a pair of output lines on which the operating voltage is made available;
N-MOS and P-MOS field effect transistor (FET) switches that automatically connect an appropriate one of the pair of input lines to an appropriate one of the pair of output lines is synchrony with positive and negative pulses of the pulsed power signal;
a filter capacitor connected between the pair of output lines; wherein said switches further comprise:
a first P-MOS FET (M1) that, when turned on, connects a first one of the input lines (LINE 1) to a first one of the output lines (V+);
a second P-MOS FET (M2) that, when turned on, connects a second one of the input lines (LINE 2) to the first one of the output lines (V+);
a first N-MOS FET (M3) that, when turned on, connects the first one of the input lines (LINE 1) to a second one of the output lines (V−);
a second N-MOS FET (M4) that, when turned on, connects the second one of the input lines (LINE 2) to the second one of the output lines (V−); and
a detector circuit that when there is a positive pulse within the pulsed power signal on LINE 1 relative to LINE 2 turns the first P-MOS FET (M1) on, the second N-MOS FET (M4) on, and maintains the second P-MOS FET (M2) off, and the first N-MOS FET (M3) off, and when there is a negative pulse within the pulsed power signal on LINE 1 relative to LINE 2, turns the second P-MOS FET (M2) on, the first N-MOS FET (M3) on and maintains the first P-MOS FET (M1) off, and the second N-MOS FET (M4) off;

wherein said detector circuit further comprises:
a first detector circuit that turns the first P-MOS FET (MI) on only when there is a positive pulse within the pulsed power signal on LINE 1 relative to LINE 2 that has an amplitude exceeding a first threshold value;
a second detector circuit that turns the second P-MOS FET (M2) on only when there is a positive pulse within the pulse power signal on LINE 2 relative to LINE 1 that has an amplitude exceeding a first threshold value;
a third detector circuit that turns the first N-MOS FET (M3) on only when there is a negative pulse within the pulse power signal on LINE 1 relative to LINE 2 that has a negative amplitude exceeding a second threshold value;
a fourth detector circuit that turns the second N-MOS FET (M4) on only when there is a negative pulse within the pulse power signal on LINE 2 relative to LINE 1 that has a negative amplitude exceeding a second threshold value;

said low power rectifier circuit wherein each of the first, second, third, and fourth detector circuits include a complementary N-MOS and P-MOS transistor pair connected as a detector circuit to be biased ON only when a pulse of the pulsed power signal present on the pair of the input lines has an amplitude greater than a bias reference voltage.

18. The implantable device of claim 17 wherein the complementary N-MOS and P-MOS transistor pair of each detector circuit has a first bias reference voltage connected to a gate terminal of its P-MOS transistor, and a second bias reference voltage connected to a gate terminal of its N-MOS transistor.

19. The implantable device of claim 18 further including a bias generator circuit that generates the first and second reference voltages, and wherein the bias generator circuit includes means for dynamically setting the first and second reference voltages to an operational level when a power signal is present on the pair of input lines, and to a low power stand-by level when a power signal is not present on the pair of input lines.

20. The implantable device of claim 18 further including a complementary N-MOS and P-MOS inverter circuit interposed between each detector circuit and the respective first/second P-MOS/N-MOS FET switch controlled by the detector circuit.

21. A low power rectifier circuit implantable device comprising:

means for receiving a pulsed power signal;

a pair of input lines on which the pulsed sower signal is received;

a pair of output lines on which the operating voltage is made available;

a filter capacitor connected between the pair of output lines;

N-MOS and P-MOS field effect transistor (FET) switches that automatically connect an appropriate one of the pair of input lines to an appropriate one of the pair of output lines in synchrony with positive and negative pulses of the pulsed power signal;

further comprising startup means for providing a voltage to the filter capacitor connected between the pair of output lines at a time when no operating voltage is present on said filter capacitor.

22. The implantable device of claim 21 wherein the startup means comprises parasitic diodes within the N-MOS FET switches, and parasitic PNP bipolar transistors within the P-MOS FET switches, which parasitic diodes and transistors are sufficiently forward biased by an initial power signal on the pair of input lines to cause an initial operating voltage derived from the initial power signal to be stored on said filter capacitor.

23. A low power rectifier circuit comprising:

means for receiving a pulsed power signal;

a pair of input lines on which the pulsed power signal is received;

a pair of output lines on which the operating voltage is made available;

N-MOS and P-MOS field effect transistor (FET) switches that automatically connect an appropriate one of the pair of input lines to an appropriate one of the pair of output lines in synchrony with positive and negative pulses of the pulsed power signal; and a filter capacitor connected between the pair of output lines;

wherein the pulsed power signal comprises a pulse train of biphasic pulses, each biphasic pulse of the pulse train having a negative pulse and a positive pulse;

wherein the frequency of the biphasic pulses in the pulse train ranges from 10 to 500,000 biphasic pulses per second, and wherein each positive and negative pulse within each biphasic pulse has a pulse width of between about 1 to 3 microseconds.

* * * * *